United States Patent
Sakamoto et al.

(10) Patent No.: US 10,392,343 B2
(45) Date of Patent: *Aug. 27, 2019

(54) POLYMERIZABLE COMPOUND, POLYMERIZABLE COMPOSITION, POLYMER, AND OPTICALLY ANISOTROPIC PRODUCT

(71) Applicant: ZEON CORPORATION, Chiyoda-ku, Tokyo (JP)

(72) Inventors: Kei Sakamoto, Tokyo (JP); Kumi Okuyama, Tokyo (JP)

(73) Assignee: ZEON CORPORATION, Chiyoda-ku, Tokyo (JP)

(*) Notice: Subject to any disclaimer, the term of this patent is extended or adjusted under 35 U.S.C. 154(b) by 302 days.

This patent is subject to a terminal disclaimer.

(21) Appl. No.: 15/114,159

(22) PCT Filed: Feb. 9, 2015

(86) PCT No.: PCT/JP2015/053533
§ 371 (c)(1),
(2) Date: Jul. 26, 2016

(87) PCT Pub. No.: WO2015/122385
PCT Pub. Date: Aug. 20, 2015

(65) Prior Publication Data
US 2017/0008833 A1    Jan. 12, 2017

(30) Foreign Application Priority Data

Feb. 12, 2014    (JP) ................. 2014-024677

(51) Int. Cl.
G02F 1/1333    (2006.01)
C07C 251/88    (2006.01)
(Continued)

(52) U.S. Cl.
CPC .......... *C07C 251/88* (2013.01); *C07C 251/86* (2013.01); *C08F 220/30* (2013.01);
(Continued)

(58) Field of Classification Search
CPC ............... C09K 19/24; C09K 19/3809; C09K 2019/0448; C08F 220/30; C08F 220/34;
(Continued)

(56) References Cited

U.S. PATENT DOCUMENTS 5,567,349 A    10/1996 Kelly et al.
6,139,771 A    10/2000 Walba et al.
(Continued)

FOREIGN PATENT DOCUMENTS

JP    H1068816 A    3/1998
JP    H1090521 A    4/1998
(Continued)

OTHER PUBLICATIONS

Aug. 16, 2016, International Preliminary Report on Patentability issued in the International Patent Application No. PCT/JP2015/053533.

(Continued)

*Primary Examiner* — Geraldina Visconti
(74) *Attorney, Agent, or Firm* — Kenja IP Law PC

(57) ABSTRACT

The present invention is a polymerizable compound represented by a general formula (I), a polymerazable composition, a polymer, and an optically anisotropic product. In the formula: $Q^1$ to $Q^4$ represent hydrogen atoms, an alkyl group having 1 to 6 carbon atoms or the like; X represents a divalent aromatic group having 6 to 12 carbon atoms or the like; $A^x$ represents a group represented by a general formula (II); $A^y$ represents a group represented by a general formula (III); n represents 0 or 1; "*" indicates a bonding position; $Y^{1x}$ to $Y^{6x}$ and $Y^{1y}$ to $Y^{8y}$ represent a chemical single bond, —O—, —S—, —O—C(=O)—, —C(=O)—O—, —O—C(=O)—O— or the like; $G^{1x}$, $G^{2x}$, $G^{1y}$ and $G^{2y}$ represent a divalent aliphatic group having 1 to 20 carbon atoms or the like; $Z^{1x}$, $Z^{2x}$, $Z^{1y}$ and $Z^{2y}$ represent an alkenyl group having 2 to 10 carbon atoms or the like; $A^{1x}$ and $A^{1y}$ represent a trivalent aromatic group or the like; $A^{2x}$, $A^{3x}$, $A^{4y}$ and $A^{5y}$ represent a divalent aromatic group having 4 to 30 carbon atoms or the like; and $A^{2y}$ and $A^{3y}$ represent a divalent alicyclic hydrocarbon group having 3 to 30 carbon atoms or the like.

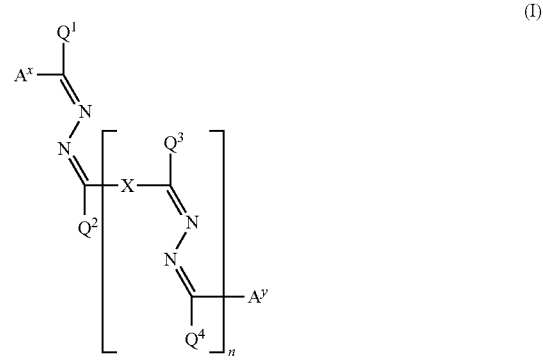

(I)

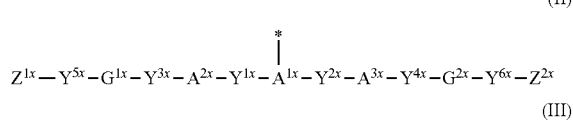

(II)

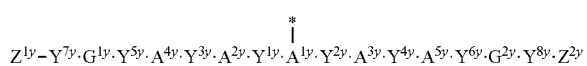

(III)

13 Claims, No Drawings

(51) Int. Cl.
*C08F 220/30* (2006.01)
*C08F 220/34* (2006.01)
*C09K 19/24* (2006.01)
*C07C 251/86* (2006.01)
*C08F 222/22* (2006.01)
*C09K 19/38* (2006.01)
*C09K 19/04* (2006.01)

(52) U.S. Cl.
CPC .......... *C08F 220/34* (2013.01); *C08F 222/22* (2013.01); *C09K 19/24* (2013.01); *C09K 19/3809* (2013.01); *C08F 2220/303* (2013.01); *C09K 2019/0448* (2013.01)

(58) Field of Classification Search
CPC ............. C08F 222/22; C08F 2220/303; C07C 251/86; C07C 251/88
USPC ........................................................ 526/312
See application file for complete search history.

(56) References Cited

U.S. PATENT DOCUMENTS

| | | | |
|---|---|---|---|
| 6,203,724 | B1 | 3/2001 | Reiffenrath et al. |
| 6,565,974 | B1 | 5/2003 | Uchiyama et al. |
| 9,029,490 | B2 | 5/2015 | Sakamoto et al. |
| 9,150,677 | B2 | 10/2015 | Sakamoto et al. |
| 9,207,360 | B2 | 12/2015 | Sakamoto et al. |
| 9,234,056 | B2 * | 1/2016 | Sakamoto .............. C09K 19/32 |
| 2002/0159005 | A1 | 10/2002 | Arakawa et al. |
| 2003/0102458 | A1 | 6/2003 | Nishikawa et al. |
| 2007/0176145 | A1 | 8/2007 | Nishikawa et al. |
| 2007/0298191 | A1 | 12/2007 | Yamahara et al. |
| 2009/0072194 | A1 | 3/2009 | Yamahara et al. |
| 2009/0189120 | A1 | 7/2009 | Takeuchi |
| 2010/0201920 | A1 | 8/2010 | Adlem et al. |
| 2010/0301271 | A1 | 12/2010 | Adlem et al. |
| 2014/0107247 | A1 | 4/2014 | Sakamoto et al. |
| 2016/0002374 | A1 * | 1/2016 | Sakamoto .............. G02B 5/3025 526/257 |

FOREIGN PATENT DOCUMENTS

| | | |
|---|---|---|
| JP | H1152131 A | 2/1999 |
| JP | 2000284126 A | 10/2000 |
| JP | 2001004837 A | 1/2001 |
| JP | 2002267838 A | 9/2002 |
| JP | 2003160540 A | 6/2003 |
| JP | 2005208414 A | 8/2005 |
| JP | 2005208415 A | 8/2005 |
| JP | 2005208416 A | 8/2005 |
| JP | 2005289980 A | 10/2005 |
| JP | 2006330710 A | 12/2006 |
| JP | 2007002208 A | 1/2007 |
| JP | 2009173893 A | 8/2009 |
| JP | 2009179563 A | 8/2009 |
| JP | 2009274984 A | 11/2009 |
| JP | 2010030979 A | 2/2010 |
| JP | 2010031223 A | 2/2010 |
| JP | 2010537954 A | 12/2010 |
| JP | 2010537955 A | 12/2010 |
| JP | 2011006360 A | 1/2011 |
| JP | 2011006361 A | 1/2011 |
| JP | 2011042606 A | 3/2011 |
| WO | 0026705 A1 | 5/2000 |
| WO | 2006052001 A1 | 5/2006 |
| WO | 2012141245 A1 | 10/2012 |
| WO | 2012147904 A1 | 11/2012 |
| WO | 2012169424 A1 | 12/2012 |
| WO | 2012176679 A1 | 12/2012 |
| WO | 2013018526 A1 | 2/2013 |
| WO | 2014061709 A1 | 4/2014 |

OTHER PUBLICATIONS

Sep. 4, 2017, Extended European Search Report issued by the European Patent Office in the corresponding European Patent Application No. 15749035.0.

May 19, 2015, International Search Report issued in the International Patent Application No. PCT/JP2015/053533.

* cited by examiner

POLYMERIZABLE COMPOUND, POLYMERIZABLE COMPOSITION, POLYMER, AND OPTICALLY ANISOTROPIC PRODUCT

TECHNICAL FIELD

The present invention relates to a polymerizable compound, a polymerizable composition, and a polymer that can produce an optical film that achieves uniform conversion of polarized light over a wide wavelength band, and also relates to an optically anisotropic product.

A flat panel display (FPD) that utilizes an optical film (e.g., polarizer and retardation film) can achieve high-resolution display, and has been widely used as a display device that exhibits excellent performance.

However, a known retardation film has a problem in that polarized light that passes through the retardation film is converted into colored polarized light. In order to solve this problem, various wideband retardation films that can achieve uniform retardation with respect to light over a wide wavelength band (i.e., retardation films having reverse wavelength dispersion) have been studied (see Patent Literature 1 to 6, for example).

It has been desired to reduce the thickness of the flat panel display as much as possible along with an improvement in performance and widespread use of mobile information terminals (e.g., mobile personal computer and mobile phone). Therefore, a reduction in thickness of the retardation film has also been desired. It has been considered that the thickness of the retardation film can be most effectively reduced by producing the retardation film by applying a polymerizable composition that includes a low-molecular-weight polymerizable compound to a film substrate. Low-molecular-weight polymerizable compounds having excellent wavelength dispersion and polymerizable compositions using such polymerizable compounds have been proposed (see Patent Literature 7 to 24).

However, the low-molecular-weight polymerizable compounds or the polymerizable compositions disclosed in Patent Literature 7 to 24 have a number of problems in that reverse wavelength dispersion may be insufficient, or it may be difficult to apply the low-molecular-weight polymerizable compounds or the polymerizable compositions to a film due to a high melting point, or the temperature range in which liquid crystallinity is obtained may be very narrow, or the solubility in a solvent normally used for an industrial process may be low. Moreover, since these low-molecular-weight polymerizable compounds and the like are synthesized by a plurality of steps using a synthesis method that utilizes an expensive reagent, an increase in cost occurs.

CITATION LIST

Patent Literature

Patent Literature 1: JP-A-10-68816
Patent Literature 2: JP-A-10-90521
Patent Literature 3: JP-A-11-52131
Patent Literature 4: JP-A-2000-284126 (US20020159005A1)
Patent Literature 5: JP-A-2001-4837
Patent Literature 6: WO2000/026705
Patent Literature 7: JP-A-2002-267838
Patent Literature 8: JP-A-2003-160540 (US20030102458A1)
Patent Literature 9: JP-A-2005-208414
Patent Literature 10: JP-A-2005-208415
Patent Literature 11: JP-A-2005-208416
Patent Literature 12: JP-A-2005-289980 (US20070176145A1)
Patent Literature 13: JP-A-2006-330710 (US20090072194A1)
Patent Literature 14: JP-A-2009-179563 (US20090189120A1)
Patent Literature 15: JP-A-2010-31223
Patent Literature 16: JP-A-2011-6360
Patent Literature 17: JP-A-2011-6361
Patent Literature 18: JP-A-2011-42606
Patent Literature 19: JP-T-2010-537954 (US20100201920A1)
Patent Literature 20: JP-T-2010-537955 (US20100301271A1)
Patent Literature 21: WO2006/052001 (US20070298191A1)
Patent Literature 22: U.S. Pat. No. 6,139,771
Patent Literature 23: U.S. Pat. No. 6,203,724
Patent Literature 24: U.S. Pat. No. 5,567,349

SUMMARY OF INVENTION

Technical Problem

The invention was conceived in view of the above situation. An object of the invention is to provide a novel polymerizable compound and the like that have practical thermal properties, exhibit excellent solubility in a general-purpose solvent, can be produced at low cost, and can produce an optical film that achieves uniform conversion of polarized light over a wide wavelength band.

Solution to Problem

The inventors conducted extensive studies in order to solve the above problem. As a result, the inventors found that a polymer having reverse wavelength dispersion can be easily obtained by copolymerizing a polymerizable compound represented by the following formula (I) and a polymerizable compound that produces a polymer having normal wavelength dispersion, and an optical film that achieves uniform conversion of polarized light over a wide wavelength band, and exhibits satisfactory performance can be produced at low cost by utilizing an optically anisotropic product produced using the resulting polymer. This finding has led to the completion of the invention.

Several aspects of the invention provide the following polymerizable compound (see (1) to (7)), polymerizable composition (see (8)), polymer (see (9)), and optically anisotropic product (see (10)).

(1) A polymerizable compound represented by the following general formula (I),

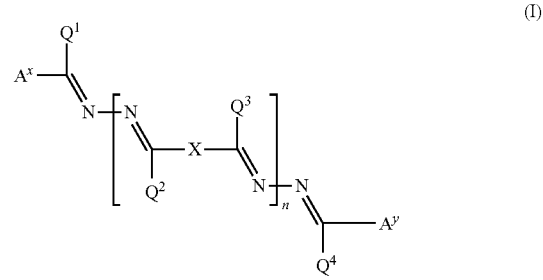

wherein each of $Q^1$ to $Q^4$ independently represents a hydrogen atom, or a substituted or unsubstituted alkyl group having 1 to 6 carbon atoms, X represents a substituted or unsubstituted divalent aromatic group having 4 to 12 carbon atoms, $A^x$ represents a group represented by the following general formula (II),

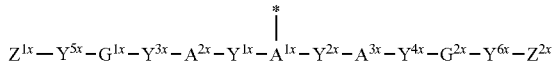

(II)

wherein "*" indicates a bonding position, each of $Y^{1x}$ to $Y^{6x}$ independently represents a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, $R^1$ represents a hydrogen atom or an alkyl group having 1 to 6 carbon atoms, each of $G^{1x}$ and $G^{2x}$ independently represents a substituted or unsubstituted divalent aliphatic group having 1 to 20 carbon atoms that optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that a case where the aliphatic group includes two or more contiguous —O— or —S— is excluded, $R^2$ represents a hydrogen atom or an alkyl group having 1 to 6 carbon atoms, each of $Z^{1x}$ and $Z^{2x}$ independently represents an alkenyl group having 2 to 10 carbon atoms that is substituted with a halogen atom, or unsubstituted, $A^{1x}$ represents a substituted or unsubstituted trivalent aromatic group, and each of $A^{2x}$ and $A^{3x}$ independently represents a substituted or unsubstituted divalent aromatic group having 4 to 30 carbon atoms, $A^y$ represents a group represented by the following general formula (III),

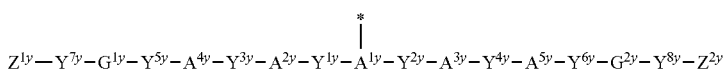

(III)

wherein each of $Y^{1y}$ to $Y^{8y}$ independently represents a chemical single bond, —O—, —S—, —O—C(=O)—, —C(=O)—O—, —O—C(=O)—O—, —NR$^3$—C(=O)—, —C(=O)—NR$^3$—, —O—C(=O)—NR$^3$—, —NR$^3$—C(=O)—O—, —NR$^3$—C(=O)—NR$^3$—, —O—NR$^3$—, or —NR$^3$—O—, $R^3$ represents a hydrogen atom or an alkyl group having 1 to 6 carbon atoms, each of $G^{1y}$ and $G^{2y}$ independently represents a substituted or unsubstituted divalent aliphatic group having 1 to 20 carbon atoms that optionally includes —O—, —S—, —O—C(=O)—, —C(=O)—O—, —O—C(=O)—O—, —NR$^4$—C(=O)—, —C(=O)—NR$^4$—, —NR$^4$—, or —C(=O)—, provided that a case where the aliphatic group includes two or more contiguous —O— or —S— is excluded, $R^4$ represents a hydrogen atom or an alkyl group having 1 to 6 carbon atoms, each of $Z^{1y}$ and $Z^{2y}$ independently represents an alkenyl group having 2 to 10 carbon atoms that is substituted with a halogen atom, or unsubstituted, $A^{1y}$ represents a substituted or unsubstituted trivalent aromatic group, each of $A^{2y}$ and $A^{3y}$ independently represents a substituted or unsubstituted divalent alicyclic hydrocarbon group having 3 to 30 carbon atoms, and each of $A^{4y}$ and $A^{5y}$ independently represents a substituted or unsubstituted aromatic group having 4 to 30 carbon atoms, and n represents 0 or 1.

(2) The polymerizable compound according to (1), wherein each of $A^{1x}$ and $A^{1y}$ is independently a substituted or unsubstituted trivalent benzene ring group, or a substituted or unsubstituted trivalent naphthalene ring group, and each of $A^{2x}$, $A^{3x}$, and $A^{2y}$ to $A^{5y}$ is independently a substituted or unsubstituted phenylene group, or a substituted or unsubstituted naphthylene group.

(3) The polymerizable compound according to (1) or (2), wherein each of $Y^{1x}$ to $Y^{6x}$ and $Y^{1y}$ to $Y^{8Y}$ is independently a chemical single bond, —O—, —O—C(=O)—, —C(=O)—O—, or —O—C(=O)—O—.

(4) The polymerizable compound according to any one of (1) to (3), wherein each of $Z^{1x}$, $Z^{2x}$, $Z^{1y}$, and $Z^{2y}$ is independently $CH_2$=CH—, $CH_2$=C($CH_3$)—, or $CH_2$=C(Cl)—.

(5) The polymerizable compound according to any one of (1) to (4), wherein each of $G^{1x}$, $G^{2x}$, $G^{1y}$, and $G^{2y}$ is independently a substituted or unsubstituted divalent aliphatic group having 1 to 12 carbon atoms that optionally includes —O—, —O—C(=O)—, —C(=O)—O—, or —C(=O)—, provided that a case where the aliphatic group includes two or more contiguous —O— is excluded.

(6) The polymerizable compound according to any one of (1) to (5), wherein X is a substituted or unsubstituted phenylene group, a substituted or unsubstituted naphthylene group, or a substituted or unsubstituted biphenylene group.

(7) The polymerizable compound according to any one of (1) to (6), wherein each of $A^{1x}$ and $A^{1y}$ is independently a substituted or unsubstituted trivalent benzene ring group, each of $A^{2x}$, $A^{3x}$, $A^{4y}$, and $A^{5y}$ is independently a substituted or unsubstituted phenylene group, each of $Y^{1x}$ to $Y^{6x}$ and $Y^{1y}$ to $Y^{8Y}$ is independently a chemical single bond, —O—, —O—C(=O)—, —C(=O)—O—, or —O—C(=O)—O—, each of $Z^{1x}$, $Z^{2x}$, $Z^{1y}$, and $Z^{2y}$ is independently $CH_2$=CH—, $CH_2$=C($CH_3$)—, or $CH_2$=C(Cl)—, and each of $G^{1x}$, $G^{2x}$, $G^{1y}$, and $G^{2y}$ is independently a divalent alkylene group having 1 to 12 carbon atoms.

(8) A polymerizable composition including at least one polymerizable compound according to any one of (1) to (7), and an initiator.

(9) A polymer obtained by polymerizing the polymerizable compound according to any one of (1) to (7), or polymerizing the polymerizable composition according to (8).

(10) An optically anisotropic product including the polymer according to (9).

Advantageous Effects of Invention

The polymerizable compound according to one aspect of the invention can provide reverse wavelength dispersion when merely added to another polymerizable compound having normal wavelength dispersion.

Therefore, it is possible to inexpensively obtain an optical film that achieves uniform conversion of polarized light over a wide wavelength band, and exhibits satisfactory performance, by utilizing the polymerizable compound according to one aspect of the invention, the polymerizable composition that utilizes the polymerizable compound, and the polymer produced using the polymerizable compound.

Since the optically anisotropic product according to one aspect of the invention includes the polymer according to one aspect of the invention, it is possible to easily and inexpensively produce an optical film that achieves uniform conversion of polarized light over a wide wavelength band, and exhibits satisfactory performance by utilizing the optically anisotropic product. Specific application examples of the optical film (optically anisotropic product) include an antireflective film that may suitably be used to prevent reflection from a touch panel or an organic electroluminescence device when used in combination with a polarizer.

A polymerizable compound, a polymerizable composition, a polymer, and an optically anisotropic product according to the exemplary embodiments of the invention are described in detail below.

1) Polymerizable compound

A polymerizable compound according to one embodiment of the invention is a compound represented by the general formula (I).

Each of $Q^1$ to $Q^4$ in the formula (I) independently represents a hydrogen atom, or a substituted or unsubstituted alkyl group having 1 to 6 carbon atoms.

Note that the expression "substituted or unsubstituted" used herein in connection with a group or the like means that the group or the like is unsubstituted, or substituted with a substituent (hereinafter the same).

Examples of the alkyl group having 1 to 6 carbon atoms (that is substituted or unsubstituted) include a methyl group, an ethyl group, an n-propyl group, an isopropyl group, an n-butyl group, a sec-butyl group, a t-butyl group, an n-pentyl group, an n-hexyl group, and the like.

Examples of a substituent that may substitute the alkyl group having 1 to 6 carbon atoms include a halogen atom such as a fluorine atom, a chlorine atom, a bromine atom, and an iodine atom; an alkoxy group having 1 to 6 carbon atoms, such as a methoxy group, an ethoxy group, an n-propoxy group, an isopropoxy group, an n-butoxy group, a sec-butoxy group, a t-butoxy group, an n-pentyloxy group, and an n-hexyloxy group; and the like. Among these, a fluorine atom, a methoxy group, and an ethoxy group are preferable.

It is preferable that each of $Q^1$ to $Q^4$ be independently a hydrogen atom or an alkyl group having 1 to 6 carbon atoms, and more preferably a hydrogen atom or a methyl group.

X in the general formula (I) represents a substituted or unsubstituted divalent aromatic group having 4 to 12 carbon atoms.

The aromatic group represented by X may be a monocyclic aromatic group, a polycyclic aromatic group, or an aromatic group in which a plurality of aromatic rings are bonded.

Examples of the aromatic group represented by X include the groups respectively represented by the following formulas. Note that "-" in the following formulas indicates a chemical bond (hereinafter the same).

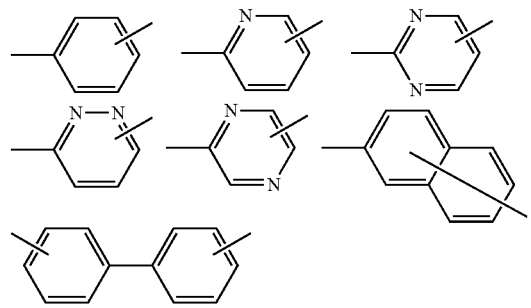

These aromatic groups may be substituted with a substituent at an arbitrary position. Examples of the substituent include a halogen atom, a cyano group, a hydroxyl group, an alkyl group having 1 to 6 carbon atoms, an alkoxy group having 1 to 6 carbon atoms, a nitro group, a —C(=O)—$OR^a$ group (wherein $R^a$ represents an alkyl group having 1 to 6 carbon atoms), and the like. Among these, a halogen atom, an alkyl group having 1 to 6 carbon atoms, and an alkoxy group having 1 to 6 carbon atoms are preferable, and a fluorine atom, an alkyl group having 1 to 3 carbon atoms, such as a methyl group, an ethyl group, and a propyl group, and an alkoxy group having 1 to 3 carbon atoms, such as a methoxy group, an ethoxy group, and a propoxy group, are more preferable.

X is preferably a substituted or unsubstituted phenylene group, a substituted or unsubstituted naphthylene group, or a substituted or unsubstituted biphenylene group, more preferably a substituted or unsubstituted phenylene group or a substituted or unsubstituted naphthylene group, still more preferably the group represented by the following formula (X1) or the group represented by the following formula (X2), and particularly preferably the group represented by the formula (X1), in order to ensure that the intended effects of the invention can be more advantageously achieved.

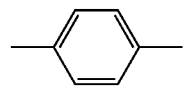 (X1)

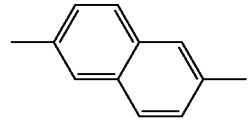 (X2)

$A^x$ in the general formula (I) represents the group represented by the general formula (II).

Each of $Y^{1x}$ to $Y^{6x}$ in the general formula (II) independently represents a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—.

$R^1$ represents a hydrogen atom or an alkyl group having 1 to 6 carbon atoms.

Examples of the alkyl group having 1 to 6 carbon atoms represented by $R^1$ include a methyl group, an ethyl group, an n-propyl group, an isopropyl group, an n-butyl group, a sec-butyl group, a t-butyl group, an n-pentyl group, an n-hexyl group, and the like.

$R^1$ is preferably a hydrogen atom or an alkyl group having 1 to 4 carbon atoms.

It is preferable that each of $Y^{1x}$ to $Y^{6x}$ be independently a chemical single bond, —O—, —O—C(=O)—, —C(=O)—O—, or —O—C(=O)—O—.

Each of $G^{1x}$ and $G^{2x}$ independently represents a substituted or unsubstituted divalent aliphatic group having 1 to 20 carbon atoms.

Examples of the divalent aliphatic group having 1 to 20 carbon atoms include an aliphatic group having a linear structure; an aliphatic group having an alicyclic structure such as a saturated cyclic hydrocarbon (cycloalkane) structure or an unsaturated cyclic hydrocarbon (cycloolefin) structure; and the like.

Examples of a substituent that may substitute the divalent aliphatic group having 1 to 20 carbon atoms include a halogen atom such as a fluorine atom, a chlorine atom, a bromine atom, and an iodine atom; an alkoxy group having 1 to 6 carbon atoms, such as a methoxy group, an ethoxy group, an n-propoxy group, an isopropoxy group, an n-butoxy group, a sec-butoxy group, a t-butoxy group, an n-pentyloxy group, and an n-hexyloxy group; and the like. Among these, a fluorine atom, a methoxy group, and an ethoxy group are preferable.

The aliphatic group optionally includes —O—, —S—, —O—C(=O)—, —C(=O)—O—, —O—C(=O)—O—, —$NR^2$—C(=O)—, —C(=O)—$NR^2$—, —$NR^2$—, or —C(=O)—, provided that a case where the aliphatic group includes two or more contiguous —O— or —S- is excluded. Among these, —O—, —O—C(=O)—, —C(=O)—O—, and —C(=O)— are preferable.

$R^2$ represents a hydrogen atom or an alkyl group having 1 to 6 carbon atoms (mentioned above in connection with $R^1$), and preferably a hydrogen atom or a methyl group.

Specific examples of the aliphatic group that includes the above group include —CH$_2$—CH$_2$—O—CH$_2$—CH$_2$—, —CH$_2$—CH$_2$—S—CH$_2$—CH$_2$—, —CH$_2$—CH$_2$—O—C(=O)—CH$_2$—CH$_2$—, —CH$_2$—CH$_2$—C(=O)—O—CH$_2$—CH$_2$—, —CH$_2$—CH$_2$—C(=O)—O—CH$_2$—, —CH$_2$—O—C(=O)—O—CH$_2$—CH$_2$—, —CH$_2$—CH$_2$—$NR^2$—C(=O)—CH$_2$—CH$_2$—, —CH$_2$—CH$_2$—C(=O)—$NR^2$—CH$_2$—, —CH$_2$—$NR^2$—CH$_2$—CH$_2$—, —CH$_2$—C(=O)—CH$_2$—, and the like.

It is preferable that each of $G^{1x}$ and $G^{2x}$ be independently a substituted or unsubstituted divalent aliphatic group having 1 to 12 carbon atoms, more preferably a substituted or unsubstituted aliphatic group having a linear structure (e.g., an alkylene group having 1 to 12 carbon atoms or an alkenylene group having 2 to 12 carbon atoms), still more preferably an alkylene group having 1 to 12 carbon atoms (e.g., methylene group, ethylene group, trimethylene group, propylene group, tetramethylene group, pentamethylene group, hexamethylene group, or octamethylene group), and particularly preferably a tetramethylene group (—(CH$_2$)$_4$—) or a hexamethylene group (—(CH$_2$)$_6$—), in order to ensure that the intended effects of the invention can be more advantageously achieved.

Each of $Z^{1x}$ and $Z^{2x}$ independently represents an alkenyl group having 2 to 10 carbon atoms that is unsubstituted, or substituted with a halogen atom.

The number of carbon atoms of the alkenyl group is preferably 2 to 6. Examples of the halogen atom that may substitute the alkenyl group represented by $Z^{1x}$ and $Z^{2x}$ include a fluorine atom, a chlorine atom, a bromine atom, and the like. Among these, a chlorine atom is preferable.

Specific examples of the alkenyl group having 2 to 10 carbon atoms represented by $Z^{1x}$ and $Z^{2x}$ include CH$_2$=CH—, CH$_2$=C(CH$_3$)—, CH$_2$=CH—CH$_2$—, CH$_3$—CH=CH—, CH$_2$=CH—CH$_2$—CH$_2$—, CH$_2$=C(CH$_3$)—CH$_2$—CH$_2$—, (CH$_3$)$_2$C=CH—CH$_2$—, (CH$_3$)$_2$C=CH—CH$_2$—CH$_2$—, CH$_2$=C(Cl)—, CH$_2$=C(CH$_3$)—CH$_2$—, CH$_3$—CH=CH—CH$_2$—, and the like.

It is preferable that each of $Z^{1x}$ and $Z^{2x}$ be independently CH$_2$=CH—, CH$_2$=C(CH$_3$)—, CH$_2$=C(Cl)—, CH$_2$=CH—CH$_2$—, CH$_2$=C(CH$_3$)—CH$_2$—, or CH$_2$=C(CH$_3$)—CH$_2$—CH$_2$—, more preferably CH$_2$=CH—, CH$_2$=C(CH$_3$)—, or CH$_2$=C(Cl)—, and still more preferably CH$_2$=CH—, in order to ensure that the intended effects of the invention can be more advantageously achieved.

$A^{1x}$ represents a substituted or unsubstituted trivalent aromatic group. The trivalent aromatic group may be a trivalent carbocyclic aromatic group, or may be a trivalent heterocyclic aromatic group. It is preferable that the trivalent aromatic group be a trivalent carbocyclic aromatic group, and more preferably a group among the trivalent benzene ring group and the trivalent naphthalene ring groups respectively represented by the following formulas. Note that the substituents $Y^{1x}$ and $Y^{2x}$ are also included in the following formulas so that the bonding state can be readily understood ($Y^{1x}$ and $Y^{2x}$ are the same as defined above (hereinafter the same)).

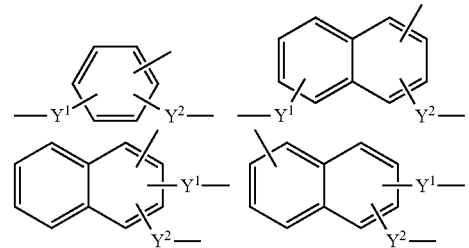

$A^{1x}$ is more preferably a group among the groups respectively represented by the following formulas (A11) to (A18), and particularly preferably the group represented by the formula (A11).

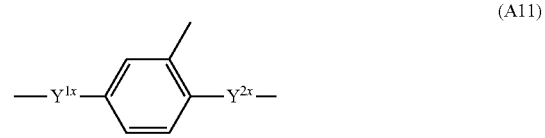

(A11)

(A12)

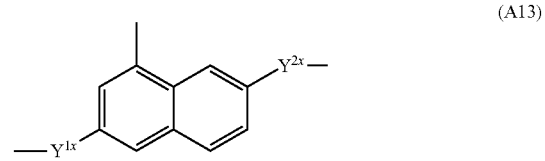

(A13)

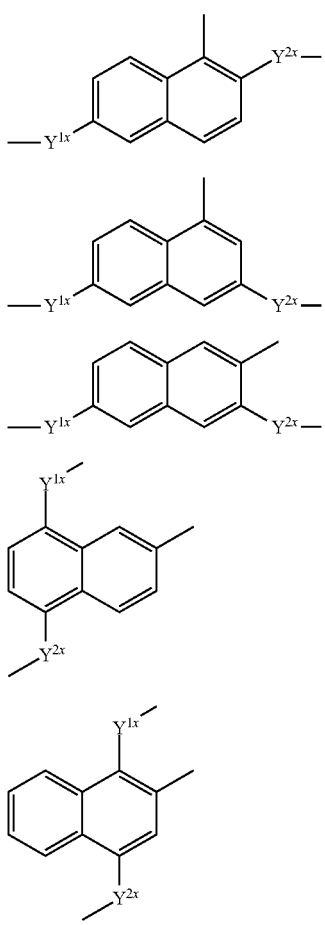

(A14)

(A15)

(A16)

(A17)

(A18)

The trivalent aromatic group represented by $A^{1x}$ may be substituted with a substituent. Examples of the substituent include a halogen atom such as a fluorine atom and a chlorine atom; a cyano group; an alkyl group having 1 to 6 carbon atoms, such as a methyl group, an ethyl group, and a propyl group; an alkenyl group having 2 to 6 carbon atoms, such as a vinyl group and an allyl group; an alkyl halide group having 1 to 6 carbon atoms, such as a trifluoromethyl group; a substituted amino group such as a dimethylamino group; an alkoxy group having 1 to 6 carbon atoms, such as a methoxy group, an ethoxy group, and an isopropoxy group; a nitro group; an aryl group such as a phenyl group and a naphthyl group; a —C(=O)—OR$^b$ group; an —SO$_2$R$_b$ group; and the like. Note that R$^b$ represents an alkyl group having 1 to 6 carbon atoms or an aryl group having 6 to 14 carbon atoms.

Each of $A^{2x}$ and $A^{3x}$ independently represents a substituted or unsubstituted divalent aromatic group having 4 to 30 carbon atoms.

The aromatic group represented by $A^{2x}$ and $A^{3x}$ may be either a monocyclic aromatic group or a polycyclic aromatic group.

Specific examples of the aromatic group represented by $A^{2x}$ and $A^{3x}$ include the following groups.

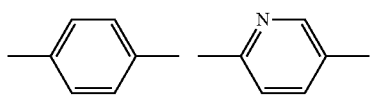

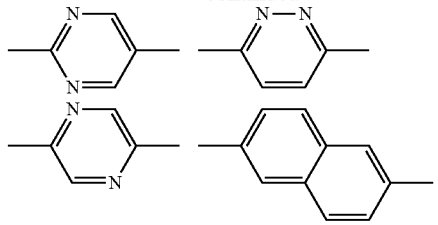

The above organic groups that may be represented by $A^{2x}$ and $A^{3x}$ may be substituted with a substituent at an arbitrary position. Examples of the substituent include a halogen atom, a cyano group, a hydroxyl group, an alkyl group having 1 to 6 carbon atoms, an alkoxy group having 1 to 6 carbon atoms, a nitro group, a —C(=O)—OR$^c$ group, and the like. Note that R$^c$ is an alkyl group having 1 to 6 carbon atoms. Among these, a halogen atom, an alkyl group having 1 to 6 carbon atoms, and an alkoxy group having 1 to 6 carbon atoms are preferable, and a fluorine atom, an alkyl group having 1 to 3 carbon atoms, such as a methyl group, an ethyl group, and a propyl group, and an alkoxy group having 1 to 3 carbon atoms, such as a methoxy group, an ethoxy group, and a propoxy group, are more preferable.

It is preferable that each of $A^{2x}$ and $A^{3x}$ be independently a substituted or unsubstituted phenylene group or a substituted or unsubstituted naphthylene group, more preferably the group represented by the following formula (A21) or (A22), and particularly preferably the group represented by the formula (A21), in order to ensure that the intended effects of the invention can be more advantageously achieved.

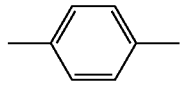

(A21)

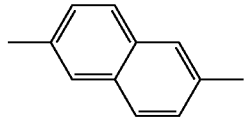

(A22)

$A^y$ in the general formula (I) represents the group represented by the general formula (III).

Each of $Y^{1y}$ to $Y^{8y}$ independently represents a chemical single bond, —O—, —S—, —O—C(=O)—, —C(=O)—O—, —O—C(=O)—O—, —NR$^3$—C(=O)—, —C(=O)—NR$^3$—, —O—C(=O)—NR$^3$—, —NR$^3$—C(=O)—O—, —NR$^3$—C(=O)—NR$^3$—, —O—NR$^3$—, or —NR$^3$—O— (mentioned above in connection with $Y^{1x}$ to $Y^{6x}$). R$^3$ represents a hydrogen atom or an alkyl group having 1 to 6 carbon atoms (mentioned above in connection with R$^1$).

Each of $G^{1y}$ and $G^{2y}$ independently represents a substituted or unsubstituted divalent aliphatic group having 1 to 20 carbon atoms (mentioned above in connection with $G^{1x}$ and $G^{2x}$).

Each of $Z^{1y}$ and $Z^{2y}$ independently represents an alkenyl group having 2 to 10 carbon atoms that is substituted with a halogen atom, or unsubstituted (mentioned above in connection with $Z^{1x}$ and $Z^{2x}$).

$A^{1y}$ represents a substituted or unsubstituted trivalent aromatic group (mentioned above in connection with $A^{1x}$).

Each of $A^{4y}$ and $A^{5y}$ independently represents a substituted or unsubstituted aromatic group having 4 to 30 carbon atoms (mentioned above in connection with $A^{2x}$ and $A^{3x}$).

Each of $A^{2y}$ and $A^{3y}$ independently represents a substituted or unsubstituted divalent alicyclic hydrocarbon group having 3 to 30 carbon atoms.

Examples of the divalent alicyclic hydrocarbon group having 3 to 30 carbon atoms include a cycloalkanediyl group having 3 to 30 carbon atoms, a divalent fused alicyclic group having 10 to 30 carbon atoms, and the like.

Examples of the cycloalkanediyl group having 3 to 30 carbon atoms include a cyclopropanediyl group; a cyclobutanediyl group such as a cyclobutane-1,2-diyl group and a cyclobutane-1,3-diyl group; a cyclopentanediyl group such as a cyclopentane-1,2-diyl group and a cyclopentane-1,3-diyl group; a cyclohexanediyl group such as a cyclohexane-1,2-diyl group, a cyclohexane-1,3-diyl group, and a cyclohexane-1,4-diyl group; a cycloheptanediyl group such as a cycloheptane-1,2-diyl group, a cycloheptane-1,3-diyl group, and a cycloheptane-1,4-diyl group; a cyclooctanediyl group such as a cyclooctane-1,2-diyl group, a cyclooctane-1,3-diyl group, a cyclooctane-1,4-diyl group, and a cyclooctane-1,5-diyl group; a cyclodecanediyl group such as a cyclodecane-1,2-diyl group, a cyclodecane-1,3-diyl group, a cyclodecane-1,4-diyl group, and a cyclodecane-1,5-diyl group; a cyclododecanediyl group such as a cyclododecane-1,2-diyl group, a cyclododecane-1,3-diyl group, a cyclododecane-1,4-diyl group, and a cyclododecane-1,5-diyl group; a cyclotetradecanediyl group such as a cyclotetradecane-1,2-diyl group, a cyclotetradecane-1,3-diyl group, a cyclotetradecane-1,4-diyl group, a cyclotetradecane-1,5-diyl group, and a cyclotetradecane-1,7-diyl group; a cycloeicosanediyl group such as a cycloeicosane-1,2-diyl group and a cycloeicosane-1,10-diyl group; and the like.

Examples of the divalent fused alicyclic group having 10 to 30 carbon atoms include a decalindiyl group such as a decalin-2,5-diyl group and a decalin-2,7-diyl group; an adamantanediyl group such as an adamantane-1,2-diyl group and an adamantane-1,3-diyl group; a bicyclo[2.2.1]heptanediyl group such as a bicyclo[2.2.1]heptane-2,3-diyl group, a bicyclo[2.2.1]heptane-2,5-diyl group, and a bicyclo[2.2.1]heptane-2,6-diyl group; and the like.

These divalent alicyclic hydrocarbon groups may be substituted with a substituent at an arbitrary position. Examples of the substituent include those mentioned above in connection with the aromatic ring included in $A^x$.

$A^{2y}$ and $A^{3y}$ are preferably a divalent alicyclic hydrocarbon group having 3 to 12 carbon atoms, more preferably a cycloalkanediyl group having 3 to 12 carbon atoms, still more preferably a group among the groups respectively represented by the following formulas (A31) to (A34), and particularly preferably the group represented by the formula (A32).

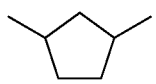
(A31)

(A32)

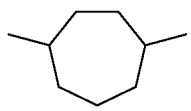
(A33)

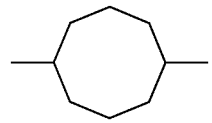
(A34)

The divalent alicyclic hydrocarbon group having 3 to 30 carbon atoms is classified into a cis-stereoisomer and a trans-stereoisomer that differ in the steric configuration of the carbon atoms bonded to $Y^{1y}$ and $Y^{3y}$ (or $Y^{2y}$ and $Y^{4y}$). For example, a cyclohexane-1,4-diyl group is classified into a cis-isomer (A32a) and a trans-isomer (A32b) (see below).

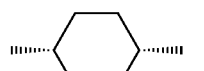
(A32a)

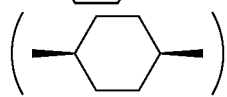
(A32b)

The divalent alicyclic hydrocarbon group having 3 to 30 carbon atoms may be a cis-isomer, a trans-isomer, or a mixture including a cis-isomer and a trans-isomer. Note that it is preferable that the divalent alicyclic hydrocarbon group having 3 to 30 carbon atoms be a trans-isomer since an excellent alignment capability can be obtained.

n in the general formula (I) represents 0 or 1, and preferably 0.

It is preferable that the polymerizable compound according to one embodiment of the invention that is represented by the formula (I) be (i) the polymerizable compound represented by the general formula (I) wherein each of $A^{1x}$ and $A^{1y}$ is independently a substituted or unsubstituted trivalent benzene ring group, or a substituted or unsubstituted trivalent naphthalene ring group, each of $A^{2x}$, $A^{3x}$, $A^{4y}$, and $A^{5y}$ is independently a substituted or unsubstituted phenylene group, or a substituted or unsubstituted naphthylene group, each of $Y^{1x}$ to $Y^{6x}$ and $Y^{1y}$ to $Y^{8y}$ is independently a chemical single bond, —O—, —O—C(=O)—, —C(=O)—O—, or —O—C(=O)—O—, each of $Z^{1x}$ to $Z^{3x}$ and $Z^{1y}$ to $Z^{3y}$ is independently $CH_2$=CH—, $CH_2$=C(CH_3)—, or $CH_2$=C(Cl)—, each of $G^{1x}$, $G^{2x}$, $G^{1y}$, and $G^{2y}$ is independently a substituted or unsubstituted divalent aliphatic group having 1 to 12 carbon atoms that optionally includes —O—, —O—C(=O)—, —C(=O)—O—, or —C(=O)—, provided that a case where the aliphatic group includes two or more contiguous —O— is excluded, and X is a substituted or unsubstituted phenylene group, a substituted or unsubstituted naphthylene group, or a substituted or unsubstituted biphenylene group, in order to ensure that the intended effects of the invention can be more advantageously achieved.

It is more preferable that the polymerizable compound according to one embodiment of the invention that is represented by the general formula (I) be (ii) the polymerizable compound represented by the general formula (I) wherein each of $A^{1x}$ and $A^{1y}$ is independently a substituted or unsubstituted trivalent benzene ring group, each of $A^{2x}$, $A^{3x}$, $A^{4y}$, and $A^{5y}$ is independently a substituted or unsubstituted phenylene group, each of $Y^{1x}$ to $Y^{6x}$ and $Y^{1y}$ to $Y^{8Y}$ is independently a chemical single bond, —O—, —O—C(=O)—, —C(=O)—O—, or —O—C(=O)—O—, each of $Z^{1x}$, $Z^{2x}$, $Z^{1y}$, and $Z^{2y}$ is independently $CH_2$=CH—, $CH_2$=C($CH_3$)—, or $CH_2$=C(Cl)—, and each of $G^{1x}$, $G^{2x}$, $G^{1y}$, and $G^{2y}$ is independently a divalent alkylene group having 1 to 12 carbon atoms.

It is particularly preferable that the polymerizable compound according to one embodiment of the invention that is represented by the general formula (I) be (iii) the polymerizable compound represented by the general formula (I) wherein n is 0, each of $A^{1x}$ and $A^{1y}$ is independently a substituted or unsubstituted trivalent benzene ring group, each of $A^{2x}$, $A^{3x}$, $A^{4y}$, and $A^{5y}$ is independently a substituted or unsubstituted phenylene group, each of $Y^{1x}$ to $Y^{6x}$ and $Y^{1y}$ to $Y^{8y}$ is independently a chemical single bond, —O—, —O—C(=O)—, —C(=O)—O—, or —O—C(=O)—O—, each of $Z^{1x}$, $Z^{2x}$, $Z^{1y}$, and $Z^{2y}$ is independently $CH_2$=CH—, $CH_2$=C($CH_3$)—, or $CH_2$=C(Cl)—, and each of $G^{1x}$, $G^{2x}$, $G^{1y}$, and $G^{2y}$ is independently a divalent alkylene group having 1 to 12 carbon atoms.

Note that the polymerizable compound represented by the general formula (I) may be a stereoisomer based on the carbon-nitrogen double bond. These stereoisomers are also intended to be included within the scope of the invention.

The polymerizable compound according to one embodiment of the invention may be produced using an arbitrary method. For example, the polymerizable compound may be produced using the following production methods.

Production Method 1

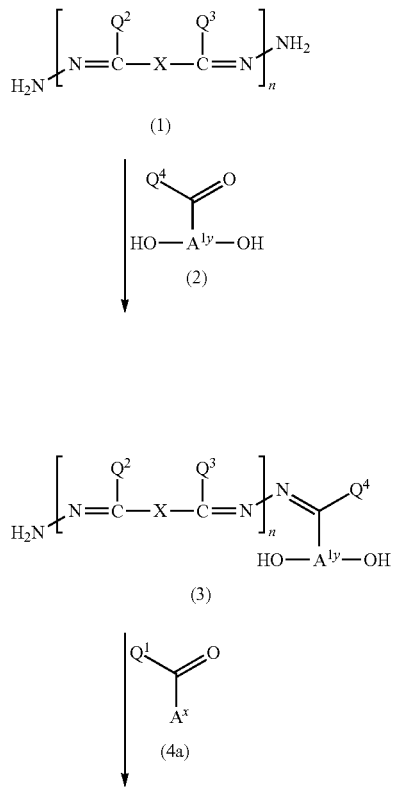

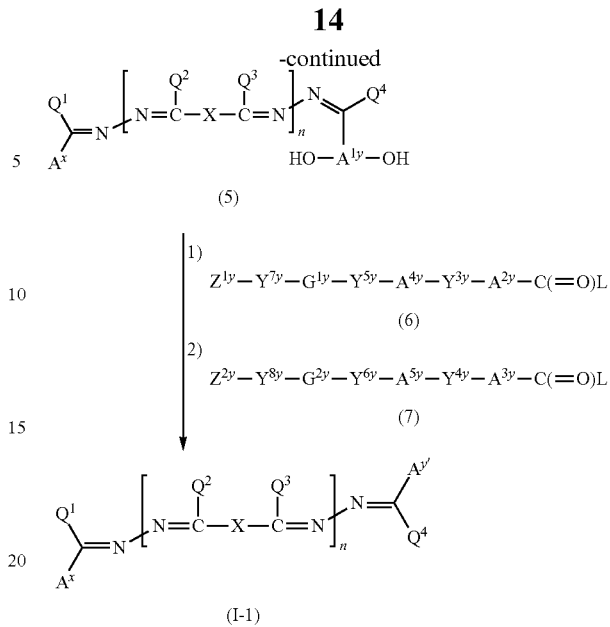

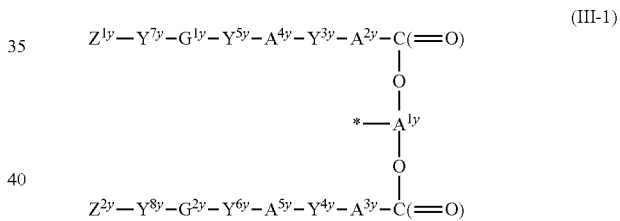

wherein $A^x$, $A^{1y}$ to $A^{5y}$, $Y^{1y}$ to $Y^{8y}$, $G^{1y}$, $G^{2y}$, $Z^{1y}$, $Z^{2y}$, $Q^1$ to $Q^4$, X, and n are the same as defined above, L represents a leaving group (e.g., hydroxyl group, halogen atom, methanesulfonyloxy group, or p-toluenesulfonyloxy group), and $A^{y''}$ represents a group represented by the following formula (III-1) wherein $Y^{1y}$ is —C(=O)—O—, and $Y^{2y}$ is —O—C(=O)— (hereinafter the same).

$$Z^{1y}-Y^{7y}-G^{1y}-Y^{5y}-A^{4y}-Y^{3y}-A^{2y}-C(=O) \atop | \atop O \atop | \atop *-A^{1y} \atop | \atop O \atop | \atop Z^{2y}-Y^{8y}-G^{2y}-Y^{6y}-A^{5y}-Y^{4y}-A^{3y}-C(=O)$$

(III-1)

Specifically, the compound represented by the formula (2) (compound (2)) is reacted with the compound represented by the formula (1) (compound (1)) in an appropriate solvent in a molar ratio (compound (2):compound (1)) of 1:1 (step 1) to obtain the compound represented by the formula (3) (compound (3)).

The carbonyl compound represented by the formula (4a) (carbonyl compound (4a)) is reacted with the compound (3) in an appropriate solvent in a molar ratio (carbonyl compound (4a):compound (3)) of 1:1 to 1:2 (preferably 1:1 to 1:1.5) (step 2) to obtain the compound represented by the formula (5) (compound (5)). The compound (5) is isolated, and sequentially reacted with the carbonyl compound represented by the formula (6) (carbonyl compound (6)) and the compound represented by the formula (7) (compound (7)) in an appropriate solvent in a molar ratio (compound (5):compound (6) (compound (7))) of 1:1.5 to 1.5:1 (steps 3 and 4) to produce the target polymerizable compound represented by the formula (I-1) (polymerizable compound (I-1)).

Note that the steps 3 and 4 may be performed after the step 2 without isolating the compound (5).

The solvent used for the above reactions is not particularly limited as long as the solvent is inert to the reactions. Examples of the solvent include an alcohol-based solvent such as methyl alcohol, ethyl alcohol, n-propyl alcohol, isopropyl alcohol, n-butyl alcohol, isobutyl alcohol, sec-butyl alcohol, tert-butyl alcohol, n-pentyl alcohol, and amyl alcohol; an ether-based solvent such as diethyl ether, tetrahydrofuran, 1,2-dimethoxyethane, 1,4-dioxane, and cyclopentyl methyl ether; an ester-based solvent such as ethyl acetate, propyl acetate, and methyl propionate; an aromatic hydrocarbon-based solvent such as benzene, toluene, and xylene; an aliphatic hydrocarbon-based solvent such as n-pentane, n-hexane, and n-heptane; an amide-based solvent such as N,N-dimethylformamide, N-methylpyrrolidone, and hexamethylphosphoric acid triamide; a sulfur-containing solvent such as dimethyl sulfoxide and sulfolane; a mixed solvent including two or more solvents among these solvents; and the like.

Among these, an alcohol-based solvent, an ether-based solvent, and a mixed solvent including an alcohol-based solvent and an ether-based solvent are preferable.

The solvent may be used in an appropriate amount taking account of the type of each compound, the reaction scale, and the like. The solvent is normally used in an amount of 1 to 100 g per gram (total mass) of the compounds used for the reaction.

The reaction proceeds smoothly when the reaction temperature is set within the range from −10° C. to the boiling point of the solvent. The reaction time is determined taking account of the reaction scale, but is normally set to several minutes to several tens of hours.

When the compound (6) and the compound (7) are identical to each other, the target polymerizable compound can be produced by reacting the compound (5) with 2-fold equivalents of the carbonyl compound (6).

Production Method 2

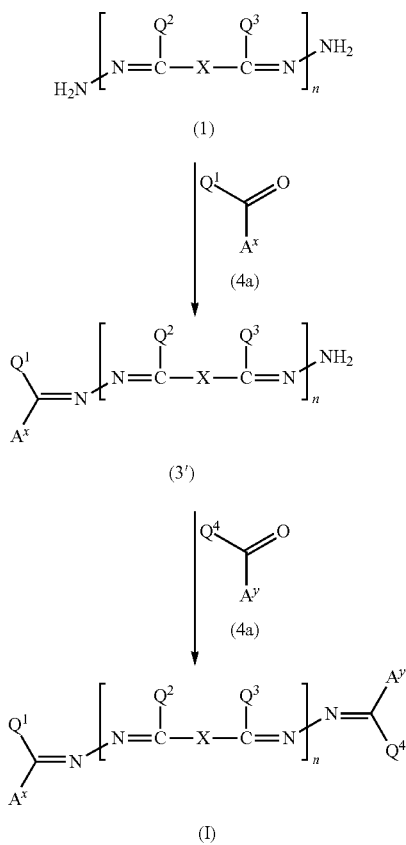

When using the production method 2, the carbonyl compound (4a) is reacted with the compound (1) in an appropriate solvent in a molar ratio (carbonyl compound (4a):compound (1)) of 1:1 to 1:1.2 to obtain the compound represented by the formula (3') (compound (3')) (step 1). The compound (3') is isolated, and reacted with the carbonyl compound represented by the formula (4b) (carbonyl compound (4b)) in an appropriate solvent in a molar ratio (compound (3'):carbonyl compound (4b)) of 1:1 to 1:1.2 (step 2) to produce the target polymerizable compound represented by the formula (I). Note that the step 2 may be performed after the step 1 without isolating the compound (3').

The above reactions may be effected substantially in the same manner as the reaction between the compound (3) and the carbonyl compound (4a).

The compound (1) wherein n is 1 (compound (1')) may be produced as described below.

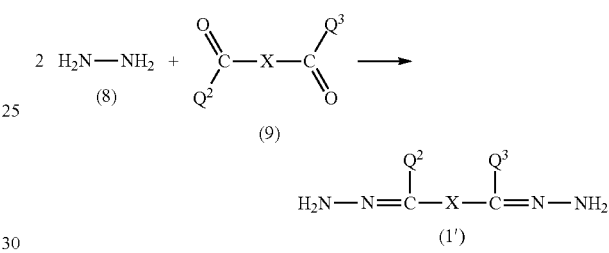

Specifically, the compound (1') may be produced by reacting the compound represented by the formula (9) (compound (9)) with 2 equivalents or more of the hydrazine (8) in an appropriate solvent.

The solvent used for the above reaction is not particularly limited as long as the solvent is inert to the reaction. Examples of the solvent include those mentioned above in connection with the method for producing the polymerizable compound (I-1).

The reaction proceeds smoothly when the reaction temperature is set within the range from −10° C. to the boiling point of the solvent. The reaction time is determined taking account of the reaction scale, but is normally set to several minutes to several hours.

When the compound (1) is hydrazine (n=0), hydrazine monohydrate is normally used as the compound (1). A commercially available product may be used directly as hydrazine.

The carbonyl compounds (4a) and (4b) may be produced by appropriately bonding and modifying a plurality of known compounds having the desired structure by arbitrarily combining an ether linkage (—O—)-forming reaction, an ester linkage (—C(=O)—O— or —O—C(=O)—)-forming reaction, a carbonate linkage (—O—C(=O)—O—)-forming reaction, and an amide linkage (—C(=O)NH— or —NHC(=O)—)-forming reaction.

An ether linkage may be formed as described below, for example.

(i) A compound represented by D1-hal (wherein hal represents a halogen atom (hereinafter the same)) and a compound represented by D2-OMet (wherein Met represents an alkali metal (mainly sodium) (hereinafter the same)) are mixed and condensed (Williamson synthesis). Note that D1 and D2 represent an arbitrary organic group (hereinafter the same).

(ii) A compound represented by D1-hal and a compound represented by D2-OH are mixed and condensed in the presence of a base (e.g., sodium hydroxide or potassium hydroxide).
(iii) A compound represented by D1-J (wherein J represents an epoxy group) and a compound represented by D2-OH are mixed and condensed in the presence of a base (e.g., sodium hydroxide or potassium hydroxide).
(iv) A compound represented by D1-ofn (wherein ofn represents a group that includes an unsaturated bond) and a compound represented by D2-OMet are mixed and subjected to an addition reaction in the presence of a base (e.g., sodium hydroxide or potassium hydroxide).
(v) A compound represented by D1-hal and a compound represented by D2-OMet are mixed and condensed in the presence of copper or cuprous chloride (Ullmann condensation).

An ester linkage and an amide linkage may be formed as described below, for example.

(vi) A compound represented by D1-COOH and a compound represented by D2-OH or D2-NH$_2$ are subjected to dehydration and condensation in the presence of a dehydration-condensation agent (e.g., N,N-dicyclohexylcarbodiimide).
(vii) A compound represented by D1-COOH is reacted with a halogenating agent to obtain a compound represented by D1-CO-hal, and the compound represented by D1-CO-hal is reacted with a compound represented by D2-OH or D2-NH$_2$ in the presence of a base.
(viii) A compound represented by D1-COOH is reacted with an acid anhydride to obtain a mixed acid anhydride, and the mixed acid anhydride is reacted with a compound represented by D2-OH or D2-NH$_2$.
(ix) A compound represented by D1-COOH and a compound represented by D2-OH or D2-NH$_2$ are subjected to dehydration and condensation in the presence of an acid catalyst or a base catalyst.

The carbonyl compound (4a) wherein the group represented by $Z^{2x}$—$Y^{6x}$-$G^{2x}$-$Y^{4x}$-$A^{3x}$-$Y^{2x}$— is identical to the group represented by $Z^{1x}$—$Y^{5x}$-$G^{1x}$-$Y^{3x}$-$A^{2x}$-$Y^{1x}$-, and $Y^{1x}$ is a group represented by —C(=O)—O—(hereinafter referred to as "compound (4')") may be produced by the following reaction.

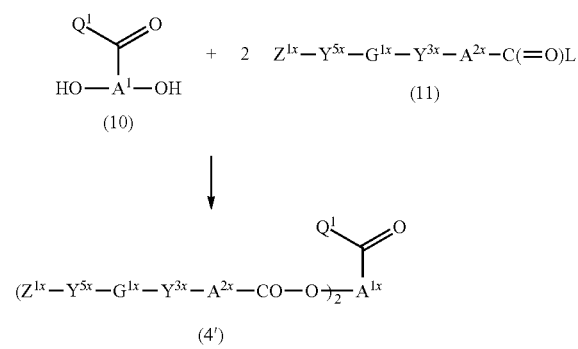

Specifically, the dihydroxy compound represented by the formula (10) (compound (10)) is reacted with the compound represented by the formula (11) (compound (11)) in a molar ratio (compound (10):compound (11)) of 1:2 to 1:4 (preferably 1:2 to 1:3) to produce the target compound (4') with high selectivity in high yield.

When the compound (11) is the compound (carboxylic acid) represented by the formula (11) wherein L is a hydroxyl group, the target product may be obtained by effecting the reaction in the presence of a dehydration-condensation agent (e.g., 1-ethyl-3-(3-dimethylaminopropyl)carbodiimide hydrochloride (WSC) or dicyclohexylcarbodiimide).

The dehydration-condensation agent is normally used in an amount of 1 to 3 mol based on 1 mol of the compound (11).

When the compound (11) is the compound (acid halide) represented by the formula (11) wherein L is a halogen atom, the target product may be obtained by effecting the reaction in the presence of a base.

Examples of the base include an organic base such as triethylamine, pyridine, and 4-(dimethylamino)pyridine, and an inorganic base such as sodium hydroxide, sodium carbonate, and sodium hydrogen carbonate.

The base is normally used in an amount of 1 to 3 mol based on 1 mol of the compound (11).

When the compound (11) is the compound (mixed acid anhydride) represented by the formula (11) wherein L is a methanesulfonyloxy group or a p-toluenesulfonyloxy group, the target product may be obtained in the same manner as in the case where L is a halogen atom.

Examples of the solvent used for the above reaction include a chlorine-based solvent such as chloroform and methylene chloride; an amide-based solvent such as N-methylpyrrolidone, N,N-dimethylformamide, N,N-dimethylacetamide, and hexamethylphosphoric triamide; an ether-based solvent such as 1,4-dioxane, cyclopentyl methyl ether, tetrahydrofuran, tetrahydropyran, and cyclopentyl methyl ether; a sulfur-containing solvent such as dimethyl sulfoxide and sulfolane; an aromatic hydrocarbon-based solvent such as benzene, toluene, and xylene; an aliphatic hydrocarbon-based solvent such as n-pentane, n-hexane, and n-octane; an alicyclic hydrocarbon-based solvent such as cyclopentane and cyclohexane; a mixed solvent including two or more solvents among these solvents; and the like.

The solvent may be used in an appropriate amount taking account of the type of each compound, the reaction scale, and the like. The solvent is normally used in an amount of 1 to 50 g per gram of the hydroxy compound (10).

The reaction proceeds smoothly when the reaction temperature is set within the range from −10° C. to the boiling point of the solvent. The reaction time is determined taking account of the reaction scale, but is normally set to several minutes to several tens of hours.

The carbonyl compound (4b) may be synthesized by reacting the compound (2) with the compound (6) and the compound (7) substantially in the same manner as in the case of synthesizing the carbonyl compound (4a).

The compound (6) and the compound (7) may be produced substantially in the same manner as the compound (11).

For example, when the compound (6) is a compound represented by the following formula (6') (compound (6')), the compound (6') may be produced as described below using a dicarboxylic acid represented by the formula (12) (compound (12)).

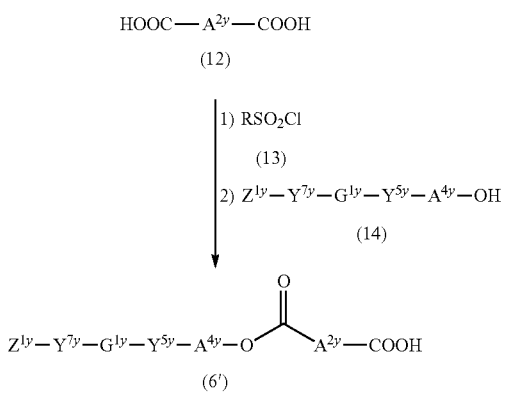

wherein R represents an alkyl group (e.g., methyl group or ethyl group) or a substituted or unsubstituted aryl group (e.g., phenyl group or p-methylphenyl group).

Specifically, the sulfonyl chloride represented by the formula (13) is reacted with the compound (12) in the presence of a base (e.g., triethylamine or 4-(dimethylamino) pyridine).

The compound (14) and a base (e.g., triethylamine or 4-(dimethylamino)pyridine) are added to the reaction mixture to effect a reaction.

The sulfonyl chloride is normally used in an amount of 0.5 to 0.7 equivalents based on 1 equivalent of the compound (12).

The compound (14) is normally used in an amount of 0.5 to 0.6 equivalents based on 1 equivalent of the compound (12).

The base is normally used in an amount of 0.5 to 0.7 equivalents based on 1 equivalent of the compound (12).

The reaction temperature is set to 20 to 30° C. The reaction time is determined taking account of the reaction scale and the like, but is normally set to several minutes to several hours.

Examples of a solvent used for the above reaction include those mentioned above in connection with the solvent that may be used when producing the compound (4'). It is preferable to use an ether as the solvent.

The solvent may be used in an appropriate amount taking account of the type of each compound, the reaction scale, and the like. The solvent is normally used in an amount of 1 to 50 g per gram of the compound (12).

After completion of the reaction, the target product is isolated by performing a post-treatment operation that is normally employed in synthetic organic chemistry, optionally followed by a known purification-separation means such as column chromatography, recrystallization, or distillation.

The structure of the target product may be identified by measurement/elemental analysis (e.g., NMR spectrometry, IR spectrometry, or mass spectrometry), and the like.

It is possible to easily obtain a polymer (preferably a liquid crystal polymer) that exhibits reverse wavelength dispersion (i.e., ideal wideband wavelength dispersion) by utilizing the polymerizable compound according to one embodiment of the invention (described later).

2) Polymerizable Composition

A polymerizable composition according to one embodiment of the invention includes at least one polymerizable compound according to one embodiment of the invention, and an initiator. The initiator is used in order to more efficiently polymerize the polymerizable compound according to one embodiment of the invention.

The initiator may be appropriately selected taking account of the type of the polymerizable group included in the polymerizable compound. For example, a radical initiator may be used when the polymerizable group is a radically polymerizable group, an anionic initiator may be used when the polymerizable group is an anionically polymerizable group, and a cationic initiator may be used when the polymerizable group is a cationically polymerizable group.

Examples of the radical initiator include a thermal radical generator that is a compound that generates active species that initiate the polymerization of the polymerizable compound upon heating, and a photo-radical generator that is a compound that generates active species that initiate the polymerization of the polymerizable compound upon exposure to exposure light (e.g., visible rays, ultraviolet rays (e.g., i-line), deep ultraviolet rays, electron beams, or X-rays). Note that it is preferable to use the photo-radical generator.

Examples of the photo-radical generator include an acetophenone-based compound, a biimidazole-based compound, a triazine-based compound, an O-acyloxime-based compound, an onium salt-based compound, a benzoin-based compound, a benzophenone-based compound, an α-diketone-based compound, a polynuclear quinone-based compound, a xanthone-based compound, a diazo-based compound, an imide sulfonate-based compound, and the like. These compounds generate either or both of active radicals and an active acid upon exposure. These photo-radical generators may be used either alone or in combination.

Specific examples of the acetophenone-based compound include 2-hydroxy-2-methyl-1-phenylpropan-1-one, 2-methyl-1-[4-(methylthio)phenyl]-2-morpholinopropan-1-one, 2-benzyl-2-dimethylamino-1-(4-morpholinophenyl)butan-1-one, 1-hydroxycyclohexyl phenyl ketone, 2,2-dimethoxy-1,2-diphenylethan-1-one, 1,2-octanedione, 2-benzyl-2-dimethylamino-4'-morpholinobutyrophenone, and the like.

Specific examples of the biimidazole-based compound include 2,2'-bis(2-chlorophenyl)-4,4',5,5'-tetrakis(4-ethoxycarbonylphenyl)-1,2'-biimidazole, 2,2'-bis(2-bromophenyl)-4,4',5,5'-tetrakis(4-ethoxycarbonylphenyl)-1,2'-biimidazole, 2,2'-bis(2-chlorophenyl)-4,4',5,5'-tetraphenyl-1,2'-biimidazole, 2,2'-bis(2,4-dichlorophenyl)-4,4',5,5'-tetraphenyl-1,2'-biimidazole, 2,2'-bis(2,4,6-trichlorophenyl)-4,4',5,5'-tetraphenyl-1,2'-biimidazole, 2,2'-bis(2-bromophenyl)-4,4',5,5'-tetraphenyl-1,2'-biimidazole, 2,2'-bis(2,4-dibromophenyl)-4,4',5,5'-tetraphenyl-1,2'-biimidazole, 2,2'-bis(2,4,6-tribromophenyl)-4,4',5,5'-tetraphenyl-1,2'-biimidazole, and the like.

When using a biimidazole-based compound as a photoinitiator, it is preferable to use a hydrogen donor in combination with the biimidazole-based compound in order to further improve sensitivity.

The term "hydrogen donor" used herein refers to a compound that can donate a hydrogen atom to radicals generated by the biimidazole-based compound upon exposure. A mercaptan-based compound (see below), an amine-based compound (see below), and the like are preferable as the hydrogen donor.

Examples of the mercaptan-based compound include 2-mercaptobenzothiazole, 2-mercaptobenzoxazole, 2-mercaptobenzimidazole, 2,5-dimercapto-1,3,4-thiadiazole, 2-mercapto-2,5-dimethylaminopyridine, and the like. Examples of the amine-based compound include 4,4'-bis(dimethylamino)benzophenone, 4,4'-bis(diethylamino)benzophenone, 4-diethylaminoacetophenone, 4-dimethylaminopropiophenone, ethyl-4-dimethylaminobenzoate, 4-dimethylaminobenzoic acid, 4-dimethylaminobenzonitrile, and the like.

Specific examples of the triazine-based compound include a triazine-based compound that includes a halomethyl group, such as 2,4,6-tris(trichloromethyl)-s-triazine, 2-methyl-4,6-bis(trichloromethyl)-s-triazine, 2-[2-(5-methylfuran-2-yl)ethenyl]-4,6-bis(trichloromethyl)-s-triazine, 2-[2-(furan-2-yl)ethenyl]-4,6-bis(trichloromethyl)-s-triazine, 2-[2-(4-diethylamino-2-methylphenyl)ethenyl]-4,6-bis(trichloromethyl)-s-triazine, 2-[2-(3,4-dimethoxyphenyl)ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, and 2-(4-n-butoxyphenyl)-4,6-bis(trichloromethyl)-s-triazine.

Specific examples of the O-acyloxime-based compound include 1-[4-(phenylthio)phenyl]heptane-1,2-dione-2-(O-benzoyloxime), 1-[4-(phenylthio)phenyl]octane-1,2-dione-2-(O-benzoyloxime), 1-[4-(benzoyl)phenyl]octane-1,2-dione-2-(O-benzoyloxime), 1-[9-ethyl-6-(2-methylbenzoyl)-9H-carbazol-3-yl]ethanone-1-(O-acetyloxime), 1-[9-ethyl-6-(3-methylbenzoyl)-9H-carbazol-3-yl]ethanone-1-(O-acetyloxime), 1-(9-ethyl-6-benzoyl-9H-carbazol-3-yl)ethanone-1-(O-acetyloxime), ethanone-1-[9-ethyl-6-(2-methyl-4-tetrahydrofuranylbenzoyl)-9H-carbazol-3-yl]-1-(O-acetyloxime), ethanone-1-[9-ethyl-6-(2-methyl-4-tetrahydropyranylbenzoyl)-9H-carbazol-3-yl]-1-(O-acetyloxime), ethanone-1-[9-ethyl-6-(2-methyl-5-tetrahydrofuranylbenzoyl)-9H-carbazol-3-yl]-1-(O-acetyloxime), ethanone-1-[9-ethyl-6-(2-methyl-5-tetrahydropyranylbenzoyl)-9H-carbazol-3-yl]-1-(O-acetyloxime), ethanone-1-[9-ethyl-6-{2-methyl-4-(2,2-dimethyl-1,3-dioxolanyl)benzoyl}-9H-carbazol-3-yl]-1-(O-acetyloxime), ethanone-1-[9-ethyl-6-(2-methyl-4-tetrahydrofuranylmethoxybenzoyl)-9H-carbazol-3-yl]-1-(O-acetyloxime), ethanone-1-[9-ethyl-6-(2-methyl-4-tetrahydropyranylmethoxybenzoyl)-9H-carbazol-3-yl]-1-(O-acetyloxime), ethanone-1-[9-ethyl-6-(2-methyl-5-tetrahydrofuranylmethoxybenzoyl)-9H-carbazol-3-yl]-1-(O-acetyloxime), ethanone-1-[9-ethyl-6-(2-methylbenzoyl)-9H-carbazol-3-yl]-1-(O-acetyloxime), ethanone-1-[9-ethyl-6-(2-methyl-5-tetrahydropyranylmethoxybenzoyl)-9H-carbazol-3-yl]-1-(O-acetyloxime), ethanone-1-[9-ethyl-6-{2-methyl-4-(2,2-dimethyl-1,3-dioxolanyl)methoxybenzoyl}-9H-carbazol-3-yl]-1-(O-acetyloxime), and the like.

A commercially available product may be used directly as the photo-radical generator. Specific examples of a commercially available product that may be used as the photo-radical generator include Irgacure 907, Irgacure 184, Irgacure 369, Irgacure 651, Irgacure 819, Irgacure 907, and Irgacure OXE02 (manufactured by BASF); Adekaoptomer N1919 (manufactured by Adeka Corporation); and the like.

Examples of the anionic initiator include an alkyllithium compound; a monolithium salt or a monosodium salt of biphenyl, naphthalene, pyrene, and the like; a polyfunctional initiator such as a dilithium salt and a trilithium salt; and the like.

Examples of the cationic initiator include a proton acid such as sulfuric acid, phosphoric acid, perchloric acid, and trifluoromethanesulfonic acid; a Lewis acid such as boron trifluoride, aluminum chloride, titanium tetrachloride, and tin tetrachloride; an aromatic onium salt or a combination of an aromatic onium salt and a reducing agent; and the like.

These initiators may be used either alone or in combination.

The initiator is normally used to prepare the polymerizable composition according to one embodiment of the invention in a ratio of 0.1 to 30 parts by weight, and preferably 0.5 to 10 parts by weight, based on 100 parts by weight of the polymerizable compound.

It is preferable to add a surfactant to the polymerizable composition according to one embodiment of the invention in order to adjust the surface tension of the polymerizable composition. The surfactant is not particularly limited. A nonionic surfactant is normally preferable as the surfactant. Examples of the nonionic surfactant include an oligomer having a molecular weight of about several thousand, such as KH-40 (manufactured by AGC Seimi Chemical Co., Ltd.). The surfactant is normally added to the polymerizable composition according to one embodiment of the invention in a ratio of 0.01 to 10 parts by weight, and preferably 0.1 to 2 parts by weight, based on 100 parts by weight of the polymerizable compound.

The polymerizable composition according to one embodiment of the invention may further include an additional additive such as an additional copolymerizable monomer (described later), a metal, a metal complex, a dye, a pigment, a fluorescent material, a phosphorescent material, a leveling agent, a thixotropic agent, a gelling agent, a polysaccharide, a UV absorber, an IR (infrared) absorber, an antioxidant, an ion-exchange resin, and a metal oxide (e.g., titanium oxide). Each additive is normally added to the polymerizable composition according to one embodiment of the invention in a ratio of 0.1 to 20 parts by weight based on 100 parts by weight of the polymerizable compound.

The polymerizable composition according to one embodiment of the invention may be prepared by mixing and dissolving given amounts of the polymerizable compound according to one embodiment of the invention, the initiator, and an optional additive in an appropriate organic solvent.

Examples of the organic solvent include a ketone such as cyclopentanone, cyclohexanone, and methyl ethyl ketone; an acetate such as butyl acetate and amyl acetate; a halogenated hydrocarbon such as chloroform, dichloromethane, and dichloroethane; an ether such as 1,4-dioxane, cyclopentyl methyl ether, tetrahydrofuran, tetrahydropyran, and 1,3-dioxolane; and the like.

The polymerizable composition thus obtained is useful as a material for producing a polymer according to one embodiment of the invention, or producing an optically anisotropic product according to one embodiment of the invention (described below).

3) Polymer

A polymer according to one embodiment of the invention is (1) a polymer obtained by polymerizing the polymerizable compound according to one embodiment of the invention, or (2) a polymer obtained by polymerizing the polymerizable composition according to one embodiment of the invention.

The term "polymerization" used herein refers to a chemical reaction in a broad sense including a normal polymerization reaction and a crosslinking reaction.

(1) Polymer Obtained by Polymerizing Polymerizable Compound

The polymer obtained by polymerizing the polymerizable compound according to one embodiment of the invention may be a homopolymer of the polymerizable compound according to one embodiment of the invention, a copolymer of two or more types of the polymerizable compounds according to one embodiment of the invention, or a copolymer of the polymerizable compound according to one embodiment of the invention and an additional copolymerizable monomer.

Examples of the additional copolymerizable monomer include a commercially available product such as LC-242 (manufactured by BASF), the compounds disclosed in JP-A-2007-002208, JP-A-2009-173893, JP-A-2009-274984, JP-A-2010-030979, JP-A-2010-031223, JP-A-2011-006360, PCT/JP2012/060011 (WO2012/141245), PCT/JP2012/061321 (WO2012/147904), PCT/JP2012/064111 (WO2012/169424), PCT/JP2012/065202 (WO2012/176679), and PCT/JP2012/067906, and the like.

Further examples of the additional copolymerizable monomer include 4'-methoxyphenyl 4-(2-methacryloyloxyethyloxy)benzoate, biphenyl 4-(6-methacryloyloxyhexyloxy)benzoate, 4'-cyanobiphenyl 4-(2-acryloyloxyethyloxy)benzoate, 4'-cyanobiphenyl 4-(2-methacryloyloxyethyloxy)benzoate, 3',4'-difluorophenyl 4-(2-methacryloyloxyethyloxy)benzoate, naphthyl 4-(2-methacryloyloxyethyloxy)benzoate, 4-acryloyloxy-4'-decylbiphenyl, 4-acryloyloxy-4'-cyanobiphenyl, 4-(2-acryloyloxyethyloxy)-4'-cyanobiphenyl, 4-(2-methacryloyloxyethyloxy)-4'-methoxybiphenyl, 4-(2-methacryloyloxyethyloxy)-4'-(4"-fluorobenzyloxy)-biphenyl, 4-acryloyloxy-4'-propylcyclohexylphenyl, 4-methacryloyl-4'-butylbicyclohexyl, 4-acryloyl-4'-amyltolane, 4-acryloyl-4'-(3,4-difluorophenyl)bicyclohexyl, (4-amylphenyl) 4-(2-acryloyloxyethyl)benzoate, (4-(4'-propylcyclohexyl)phenyl) 4-(2-acryloyloxyethyl)benzoate, and the like.

A polyfunctional monomer that includes a plurality of polymerizable unsaturated groups (e.g., acryloyl group, methacryloyl group, vinyl group, and allyl group) may also be used as the additional copolymerizable monomer.

Examples of such a polyfunctional monomer include an alkanediol diacrylate such as 1,2-butanediol diacrylate, 1,3-butanediol diacrylate, 1,4-butanediol diacrylate, neopentanediol diacrylate, and 1,6-hexanediol diacrylate; an alkanediol dimethacrylate such as 1,2-butanediol dimethacrylate, 1,3-butanediol dimethacrylate, 1,4-butanediol dimethacrylate, neopentanediol dimethacrylate, and 1,6-hexanediol dimethacrylate; a (poly)ethylene glycol diacrylate such as ethylene glycol diacrylate, diethylene glycol diacrylate, triethylene glycol diacrylate, and tetraethylene glycol diacrylate; a (poly)propylene glycol diacrylate such as propylene glycol diacrylate, dipropylene glycol diacrylate, tripropylene glycol diacrylate, and tetrapropylene glycol diacrylate; a (poly)ethylene glycol dimethacrylate such as ethylene glycol dimethacrylate, diethylene glycol dimethacrylate, triethylene glycol dimethacrylate, and tetraethylene glycol dimethacrylate; a (poly)propylene glycol dimethacrylate such as propylene glycol dimethacrylate, dipropylene glycol dimethacrylate, tripropylene glycol dimethacrylate, and tetrapropylene glycol dimethacrylate; a (poly)ethylene glycol divinyl ether such as ethylene glycol divinyl ether, diethylene glycol divinyl ether, triethylene glycol divinyl ether, and tetraethylene glycol divinyl ether; a (poly)ethylene glycol diallyl ether such as ethylene glycol diallyl ether, diethylene glycol diallyl ether, triethylene glycol diallyl ether, and tetraethylene glycol diallyl ether; bisphenol F ethoxylate diacrylate; bisphenol F ethoxylate dimethacrylate; bisphenol A ethoxylate diacrylate; bisphenol A ethoxylate dimethacrylate; trimethylolpropane triacrylate; trimethylolpropane trimethacrylate; trimethylolpropane ethoxylate triacrylate; trimethylolpropane ethoxylate trimethacrylate; trimethylolpropane propoxylate triacrylate; trimethylolpropane propoxylate trimethacrylate; isocyanuric acid ethoxylate triacrylate; glycerol ethoxylate triacrylate; glycerol propoxylate triacrylate; pentaerythritol ethoxylate tetraacrylate; ditrimethylolpropane ethoxylate tetraacrylate; dipentaerythritol ethoxylate hexaacrylate; and the like.

The polymerizable compound according to one embodiment of the invention may be (co)polymerized optionally together with the additional copolymerizable monomer in the presence of an appropriate initiator. The initiator may be used in a ratio identical to that of the initiator included in the polymerizable composition.

It is possible to easily obtain a polymer (preferably a liquid crystal polymer) that exhibits reverse wavelength dispersion (i.e., ideal wideband wavelength dispersion) by utilizing the polymerizable compound according to one embodiment of the invention and the additional copolymerizable monomer in combination. Specifically, even when a polymer obtained by polymerizing an additional polymerizable compound exhibits normal wavelength dispersion, it is possible to easily obtain a polymer (preferably a liquid crystal polymer) that exhibits reverse wavelength dispersion by copolymerizing the additional polymerizable compound with the polymerizable compound according to one embodiment of the invention.

The polymerizable compound according to one embodiment of the invention and the additional monomer are normally used in a weight ratio of 1:9 to 9:1, preferably 2:8 to 8:2, and more preferably 3:7 to 7:3.

The polymer (1) may be produced by (A) (co)polymerizing the polymerizable compound optionally together with the additional copolymerizable monomer in an appropriate organic solvent in the presence of an appropriate initiator, isolating the target polymer, dissolving the polymer in an appropriate organic solvent to prepare a solution, applying the solution to an appropriate substrate to obtain a film, and drying the film, followed by optional heating, or (B) applying a solution prepared by dissolving the polymerizable compound and an initiator in an organic solvent optionally together with the additional copolymerizable monomer to a substrate using a known coating method, removing the solvent, and effecting polymerization by applying heat or activated energy rays, for example.

Examples of the initiator include those mentioned above in connection with the initiator included in the polymerizable composition.

The organic solvent used for the polymerization reaction when implementing the method (A) is not particularly limited as long as the organic solvent is inert. Examples of the organic solvent include an aromatic hydrocarbon such as toluene, xylene, and mesitylene; a ketone such as cyclohexanone, cyclopentanone, and methyl ethyl ketone; an acetate such as butyl acetate and amyl acetate; a halogenated hydrocarbon such as chloroform, dichloromethane, and dichloroethane; an ether such as cyclopentyl methyl ether, tetrahydrofuran, and tetrahydropyran; and the like. It is preferable to use a compound having a boiling point of 60 to 250° C., and more preferably 60 to 150° C., from the viewpoint of handling capability.

Examples of the organic solvent used to dissolve the polymer when implementing the method (A) include a ketone-based solvent such as acetone, methyl ethyl ketone, methyl isobutyl ketone, cyclopentanone, and cyclohexanone; an ester-based solvent such as butyl acetate and amyl acetate; a halogenated hydrocarbon-based solvent such as dichloromethane, chloroform, and dichloroethane; an ether-based solvent such as tetrahydrofuran, tetrahydropyran, 1,2-dimethoxyethane, 1,4-dioxane, cyclopentyl methyl ether, and 1,3-dioxolane; and the like.

Examples of the organic solvent used when implementing the method (B) include a ketone-based solvent such as acetone, methyl ethyl ketone, methyl isobutyl ketone, cyclopentanone, and cyclohexanone; an ester-based solvent such as butyl acetate and amyl acetate; a halogenated hydrocarbon-based solvent such as dichloromethane, chloroform, and dichloroethane; an ether-based solvent such as tetrahydrofuran (THF), tetrahydropyran, 1,2-dimethoxyethane, 1,4-dioxane, cyclopentyl methyl ether, 1,3-dioxolane; and the like. Among these, a compound having a boiling point of 60 to 200° C. is preferable from the viewpoint of handling capability.

A substrate formed of a known organic or inorganic material may be used as the substrate. Examples of the organic material include a polycycloolefin (e.g., Zeonex and Zeonor (registered trademark) (manufactured by Zeon Corporation); Arton (registered trademark) (manufactured by JSR Corporation); and Apel (registered trademark) (manufactured by Mitsui Chemicals Inc.)), polyethylene terephthalate, a polycarbonate, a polyimide, a polyamide, polymethyl methacrylate, polystyrene, polyvinyl chloride, polytetrafluoroethylene, cellulose, cellulose triacetate, polyethersulfone, and the like. Examples of the inorganic material include silicon, glass, calcite, and the like. It is preferable to use an organic material.

The substrate may be a single-layer substrate, or may be a laminate.

The substrate is preferably a substrate formed of an organic material, and more preferably a resin film that is formed of the organic material.

The polymer solution (method (A)) or the solution subjected to polymerization (method (B)) may be applied to the substrate using a known coating method. Examples of the coating method include a curtain coating method, an extrusion coating method, a roll coating method, a spin coating method, a dip coating method, a bar coating method, a spray coating method, a slide coating method, a print coating method, and the like.

(2) Polymer Obtained by Polymerizing Polymerizable Composition

The polymer according to one embodiment of the invention can be easily obtained by polymerizing the polymerizable composition according to one embodiment of the invention. It is preferable to use the polymerizable composition that includes the initiator (particularly a photoinitiator) in order to more efficiently effect polymerization.

Specifically, it is preferable to produce the polymer according to one embodiment of the invention using the method (B) that applies the polymerizable composition according to one embodiment of the invention to a substrate, and polymerizes the applied polymerizable composition. Examples of the substrate include a substrate used to produce an optically anisotropic product (described later), and the like.

The polymerizable composition according to one embodiment of the invention may be applied to the substrate using a known coating method (e.g., bar coating method, spin coating method, roll coating method, gravure coating method, spray coating method, die coating method, cap coating method, or dipping method). A known organic solvent may be added to the polymerizable composition according to one embodiment of the invention in order to improve the applicability of the polymerizable composition. In this case, it is preferable to remove the organic solvent by natural drying, drying by heating, drying under reduced pressure, drying by heating under reduced pressure, or the like, after applying the polymerizable composition to the substrate.

The polymerizable compound according to one embodiment of the invention or the polymerizable composition according to one embodiment of the invention may be polymerized by applying activated energy rays, or utilizing a thermal polymerization method, for example. It is preferable to polymerize the polymerizable compound or the polymerizable composition by applying activated energy rays since heating is unnecessary (i.e., the reaction can be effected at room temperature). It is preferable to apply light (e.g., ultraviolet rays) to the polymerizable compound or the polymerizable composition since the operation is simple.

The temperature during application of light (irradiation) is preferably set to 30° C. or less. The UV irradiance is normally set to 1 W/m$^2$ to 10 kW/m$^2$, and preferably 5 W/m$^2$ to 2 kW/m$^2$.

A polymer obtained by polymerizing the polymerizable compound according to one embodiment of the invention or the polymerizable composition according to one embodiment of the invention may be removed from the substrate, and used alone, or may be used directly as an optical film organic material or the like without removing it from the substrate.

The number average molecular weight of the polymer according to one embodiment of the invention thus obtained is preferably 500 to 500,000, and more preferably 5000 to 300,000. When the number average molecular weight of the polymer is within the above range, the resulting film exhibits high hardness and an excellent handling capability. The number average molecular weight of the polymer may be measured by gel permeation chromatography (GPC) using monodisperse polystyrene as a standard (eluent: tetrahydrofuran (THF)).

It is considered that the polymer according to one embodiment of the invention has a structure in which crosslinking points are uniformly present within the molecule, and exhibits a high crosslinking efficiency and excellent hardness.

The polymer according to one embodiment of the invention makes it possible to inexpensively produce an optical film that achieves uniform conversion of polarized light over a wide wavelength band, and exhibits satisfactory performance.

4) Optically Anisotropic Product

An optically anisotropic product according to one embodiment of the invention includes (is produced using) the polymer according to one embodiment of the invention.

The optically anisotropic product according to one embodiment of the invention may be obtained by forming an alignment film on a substrate, and forming a liquid crystal layer on the alignment film using the polymer according to one embodiment of the invention.

The alignment film is formed on the surface of the substrate in order to achieve the in-plane alignment of an organic semiconductor compound in one direction.

The alignment film includes a polymer such as a polyimide, polyvinyl alcohol, polyester, polyallylate, polyamideimide, or polyetherimide. The alignment film may be obtained by applying a solution (alignment film-forming composition) that includes such a polymer to the substrate to form a film, drying the film, and performing a rubbing treatment in one direction, for example.

The thickness of the alignment film is preferably 0.001 to 5 μm, and more preferably 0.001 to 1 μm.

The rubbing treatment may be performed on the alignment film or the substrate. The rubbing treatment may be implemented using an arbitrary method. For example, the alignment film may be rubbed in a given direction using a roll around which a cloth or felt formed of synthetic fibers (e.g., nylon) or natural fibers (e.g., cotton) is wound. It is preferable to wash (clean) the alignment film with isopropyl alcohol or the like after completion of the rubbing treatment in order to remove a fine powder (foreign substance) formed during the rubbing treatment, and clean the surface of the alignment film.

The alignment film may be provided with a function of achieving the in-plane alignment of a cholesteric liquid crystal layer in one direction by applying polarized ultraviolet rays to the surface of the alignment film.

The liquid crystal layer may be formed on the alignment film using the polymer according to one embodiment of the invention by utilizing the method described above in connection with the polymer according to one embodiment of the invention.

Since the optically anisotropic product according to one embodiment of the invention is produced using the polymer according to one embodiment of the invention, the optically anisotropic product can be produced at low cost, achieves uniform conversion of polarized light over a wide wavelength band, and exhibits satisfactory performance.

Examples of the application of the optically anisotropic product according to one embodiment of the invention include a retardation film, an alignment film for a liquid crystal display device (liquid crystal display), a polarizer, a viewing angle enhancement film, a color filter, a low-pass filter, an optical polarization prism, an optical filter, and the like.

EXAMPLES

The invention is further described below by way of examples. Note that the invention is not limited to the following examples.

Example 1

Synthesis of Compound 1

Compound 1

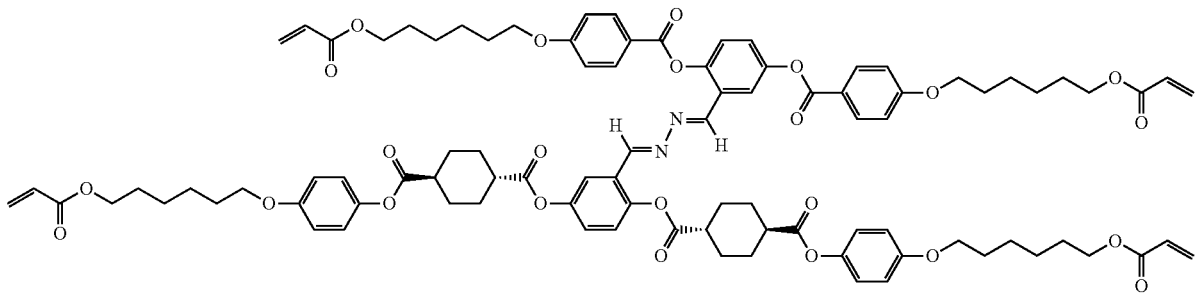

Step 1: Synthesis of Intermediate A

Intermediate A

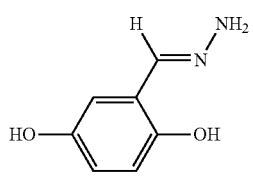

A four-necked reactor equipped with a thermometer was charged with 5.3 ml (109 mmol) of hydrazine monohydrate and 25 ml of 2-propanol under a nitrogen stream to prepare a solution. After the addition of 3.00 g (21.7 mmol) of 2,5-dihydroxybenzaldehyde to the solution, the mixture was stirred at 25° C. for 30 minutes. After completion of the reaction, a solid precipitate was filtered off by suction filtration. The solid was washed with 2-propanol, and airdried to obtain 1.82 g of an intermediate A as a white solid (yield: 55.1%). The intermediate A was used directly for the subsequent reaction without purification.

The structure of the target product was identified by $^1$H-NMR and $^{13}$C-NMR.

The $^1$H-NMR spectrum data and the $^{13}$C-NMR spectrum data are shown below. $^1$H-NMR (500 MHz, DMSO-$d_6$, TMS, δ ppm): 10.59 (brs, 1H), 8.75 (brs, 1H), 7.82 (s, 1H), 6.81 (s, 2H), 6.617 (d, 1H, J=3.0 Hz), 6.615 (d, 1H, J=9.0 Hz), 6.54 (dd, 1H, J=3.0 Hz, 9.0 Hz)

$^{13}$C-NMR (125 MHz, DMSO-$d_6$, TMS, δ ppm): 149.5, 149.1, 141.4, 119.9, 116.1, 115.6, 113.6

Step 2: Synthesis of Intermediate B

A three-necked reactor equipped with a thermometer was charged with 17.98 g (104.42 mmol) of trans-1,4-cyclohexanedicarboxylic acid and 180 ml of tetrahydrofuran (THF) under a nitrogen stream. After the addition of 6.58 g (57.43 mmol) of methanesulfonyl chloride to the mixture, the reactor was immersed in a water bath to adjust the temperature of the reaction mixture to 20° C. 6.34 g (62.65 mmol) of triethylamine was added dropwise to the reaction mixture over 10 minutes while maintaining the temperature of the reaction mixture at 20 to 30° C. After the dropwise addition, the mixture was stirred at 25° C. for 2 hours.

After the addition of 0.64 g (5.22 mmol) of 4-(dimethylamino)pyridine and 13.80 g (52.21 mmol) of 4-(6-acryloy- Intermediate B

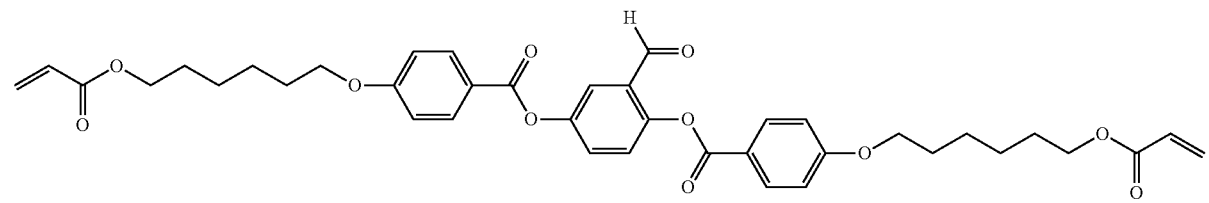

A four-necked reactor equipped with a thermometer was charged with 20 g (144.8 mmol) of 2,5-dihydroxybenzaldehyde, 105.8 g (362.0 mmol) of 4-(6-acryloylhex-1-yloxy) benzoic acid (manufactured by DKSH Japan K.K.), 5.3 g (43.4 mmol) of 4-(dimethylamino)pyridine, and 200 ml of N-methylpyrrolidone under a nitrogen stream to prepare a homogeneous solution. After the addition of 83.3 g (434.4 mmol) of 1-ethyl-3-(3-dimethylaminopropyl)carbodiimide hydrochloride (WSC) to the solution, the mixture was stirred at 25° C. for 12 hours. After completion of the reaction, the reaction mixture was added to 1.5 l of water, followed by extraction with 500 ml of ethyl acetate. The ethyl acetate layer was dried over anhydrous sodium sulfate, and sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1 (volume ratio (hereinafter the same))) to obtain 75 g of an intermediate B as a white solid (yield: 75.4%).

The structure of the target product was identified by $^1$H-NMR.

$^1$H-NMR (400 MHz, CDCl$_3$, TMS, δ ppm): 10.20 (s, 1H), 8.18-8.12 (m, 4H), 7.78 (d, 1H, J=2.8 Hz), 7.52 (dd, 1H, J=2.8 Hz, 8.7 Hz), 7.38 (d, 1H, J=8.7 Hz), 7.00-6.96 (m, 4H), 6.40 (dd, 2H, J=1.4 Hz, 17.4 Hz), 6.12 (dd, 2H, J=10.6 Hz, 17.4 Hz), 5.82 (dd, 2H, J=1.4 Hz, 10.6 Hz), 4.18 (t, 4H, J=6.4 Hz), 4.08-4.04 (m, 4H), 1.88-1.81 (m, 4H), 1.76-1.69 (m, 4H), 1.58-1.42 (m, 8H)

Step 3: Synthesis of Intermediate C loxyhex-1-yloxy)phenol (manufactured by DKSH) to the reaction mixture, the reactor was immersed in a water bath to adjust the temperature of the reaction mixture to 15° C. 6.34 g (62.65 mmol) of triethylamine was added dropwise to the reaction mixture over 10 minutes while maintaining the temperature of the reaction mixture at 20 to 30° C. After the dropwise addition, the mixture was stirred at 25° C. for 2 hours. After completion of the reaction, 1,000 ml of distilled water and 100 ml of a saturated sodium chloride solution were added to the reaction mixture, followed by extraction twice with 400 ml of ethyl acetate. The organic layer was collected, and dried over anhydrous sodium sulfate, and sodium sulfate was filtered off. The solvent was evaporated from the filtrate using a rotary evaporator, and the residue was purified by silica gel column chromatography (THF: toluene=1:9) to obtain 14.11 g of an intermediate C as a white solid (yield: 65%).

The structure of the target product was identified by $^1$H-NMR.

$^1$H-NMR (500 MHz, DMSO-$d_6$, TMS, δ ppm): 12.12 (s, 1H), 6.99 (d, 2H, J=9.0 Hz), 6.92 (d, 2H, J=9.0 Hz), 6.32 (dd, 1H, J=1.5 Hz, 17.5 Hz), 6.17 (dd, 1H, J=10.0 Hz, 17.5 Hz), 5.93 (dd, 1H, J=1.5 Hz, 10.0 Hz), 4.11 (t, 2H, J=6.5 Hz), 3.94 (t, 2H, J=6.5 Hz), 2.48-2.56 (m, 1H), 2.18-2.26 (m, 1H), 2.04-2.10 (m, 2H), 1.93-2.00 (m, 2H), 1.59-1.75 (m, 4H), 1.35-1.52 (m, 8H)

Intermediate C

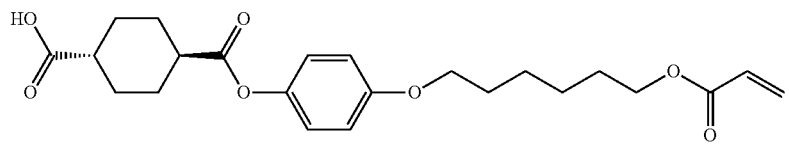

Step 4: Synthesis of Intermediate D

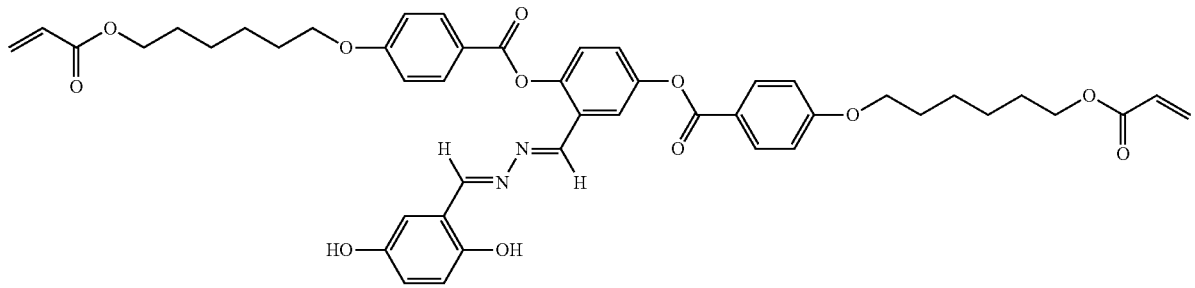

Intermediate D

A four-necked reactor equipped with a thermometer was charged with 780 mg (6.49 mmol) of the intermediate A synthesized in the step 1, 4.55 g (6.18 mmol) of the intermediate B synthesized in the step 2, 3 ml of ethanol, and 20 ml of THF under a nitrogen stream to prepare a solution. After the addition of 69.7 mg (0.30 mmol) of (±)-10-camphorsulfonic acid to the solution, the mixture was stirred at 25° C. for 1 hour. After completion of the reaction, the reaction mixture was added to 200 ml of water, followed by extraction with 400 ml of ethyl acetate. The ethyl acetate layer was dried over anhydrous sodium sulfate, and sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=90:10) to obtain 1.77 g of a intermediate D as a yellow solid (yield: 34.9%).

The structure of the target product was identified by $^1$H-NMR.

$^1$H-NMR (500 MHz, DMSO-$d_6$, TMS, δ ppm): 10.17 (s, 1H), 9.03 (s, 1H), 8.71 (s, 1H), 8.68 (s, 1H), 8.15 (d, 2H, J=9.0 Hz), 8.12 (d, 2H, J=9.0 Hz), 7.94 (d, 1H, J=3.0 Hz), 7.55 (dd, 1H, J=3.0 Hz, 8.5 Hz), 7.51 (d, 1H, J=8.5 Hz), 7.15 (d, 2H, J=9.0 Hz), 7.14 (d, 2H, J=9.0 Hz), 7.02 (d, 1H, J=3.0 Hz), 6.81 (dd, 1H, J=3.0 Hz, 9.0 Hz), 6.75 (d, 1H, J=9.0 Hz), 6.33 (dd, 2H, J=1.5 Hz, 17.5 Hz), 6.18 (dd, 2H, J=10.5 Hz, 17.5 Hz), 5.94 (dd, 2H, J=1.5 Hz, 10.5 Hz), 4.13 (t, 4H, J=6.5 Hz), 4.11 (t, 4H, J=6.5 Hz), 1.74-1.81 (m, 4H), 1.63-1.68 (m, 4H), 1.38-1.50 (m, 8H)

Step 5: Synthesis of Compound 1

A three-necked reactor equipped with a thermometer was charged with 1.31 g (3.14 mmol) of the intermediate C synthesized in the step 3 and 20 ml of THF under a nitrogen stream. After the addition of 378 mg (0.786 mmol) of methanesulfonyl chloride to the mixture, the reactor was immersed in a water bath to adjust the temperature of the reaction mixture to 20° C. 334 mg (3.30 mmol) of triethylamine was slowly added dropwise to the reaction mixture while maintaining the temperature of the reaction mixture at 20 to 30° C. After the dropwise addition, the mixture was stirred at 25° C. for 2 hours.

After the addition of 48.0 mg (0.393 mmol) of 4-(dimethylamino)pyridine and 645 mg (0.786 mmol) of the intermediate D synthesized in the step 4 to the reaction mixture, the reactor was immersed in a water bath to adjust the temperature of the reaction mixture to 15° C. 239 mg (2.36 mmol) of triethylamine was slowly added dropwise to the reaction mixture while maintaining the temperature of the reaction mixture at 20 to 30° C. After the dropwise addition, the mixture was stirred at 25° C. for 2 hours. After completion of the reaction, 100 ml of distilled water was added to the reaction mixture, followed by extraction twice with 100 ml of ethyl acetate. The ethyl acetate layer was collected, and dried over anhydrous sodium sulfate, and sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=90:10) to obtain 771 mg of a compound 1 as a white solid (yield: 60.5%).

The structure of the target product was identified by $^1$H-NMR.

$^1$H-NMR (500 MHz, CDCl$_3$, TMS, δ ppm): 8.72 (s, 1H), 8.57 (s, 1H), 8.19 (d, 2H, J=9.0 Hz), 8.16 (d, 2H, J=9.0 Hz), 8.07 (d, 1H, J=3.0 Hz), 7.79 (d, 1H, J=3.0 Hz), 7.39 (dd, 1H, J=3.0 Hz, 9.0 Hz), 7.31 (d, 1H, J=9.0 Hz), 7.18 (dd, 1H, J=3.0 Hz, 8.5 Hz), 7.13 (d, 1H, J=8.5 Hz), 7.01 (d, 2H, J=8.5 Hz), 6.96-6.99 (m, 6H), 6.87 (d, 4H, J=9.0 Hz), 6.38-6.43 (m, 4H), 6.09-6.16 (m, 4H), 5.81-5.84 (m, 4H), 4.184 (t, 4H, J=6.5 Hz), 4.175 (t, 4H, J=6.5 Hz), 4.07 (t, 2H, J=6.5 Hz), 4.05 (t, 2H, J=6.5 Hz), 3.94 (t, 4H, J=6.5 Hz), 2.50-2.73 (m, 4H), 2.24-2.31 (m, 8H), 1.76-1.92 (m, 8H), 1.61-1.74 (m, 16H), 1.42-1.57 (m, 16H)

Synthesis Example 1

Synthesis of Compound α

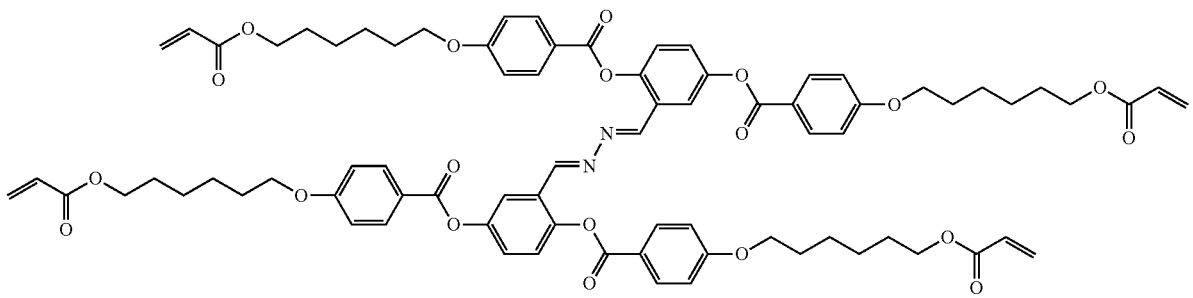

Compound α

Step 1: Synthesis of Intermediate E

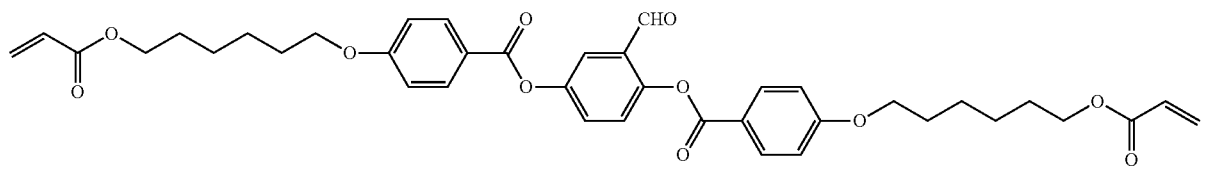

Intermediate E

A four-necked reactor equipped with a thermometer was charged with 20 g (144.8 mmol) of 2,5-dihydroxybenzaldehyde, 105.8 g (362.0 mmol) of 4-(6-acryloylhex-1-yloxy) benzoic acid (manufactured by DKSH Japan K.K.), 5.3 g (43.4 mmol) of 4-(dimethylamino)pyridine, and 200 ml of N-methylpyrrolidone under a nitrogen stream to prepare a solution. After the addition of 83.3 g (434.4 mmol) of 1-ethyl-3-(3-dimethylaminopropyl)carbodiimide hydrochloride (WSC) to the solution, the mixture was stirred at 25° C. for 12 hours. After completion of the reaction, the reaction mixture was added to 1.5 l of water, followed by extraction with 500 ml of ethyl acetate. The ethyl acetate layer was dried over anhydrous sodium sulfate, and sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1) to obtain 75 g of an intermediate E as a white solid (yield: 75.4%).

The structure of the target product was identified by $^1$H-NMR.

$^1$H-NMR (400 MHz, CDCl$_3$, TMS, δ ppm): 10.20 (s, 1H), 8.18-8.12 (m, 4H), 7.78 (d, 1H, J=2.8 Hz), 7.52 (dd, 1H, J=2.8 Hz, 8.7 Hz), 7.38 (d, 1H, J=8.7 Hz), 7.00-6.96 (m, 4H), 6.40 (dd, 2H, J=1.4 Hz, 17.4 Hz), 6.12 (dd, 2H, J=10.6 Hz, 17.4 Hz), 5.82 (dd, 2H, J=1.4 Hz, 10.6 Hz), 4.18 (t, 4H, J=6.4 Hz), 4.08-4.04 (m, 4H), 1.88-1.81 (m, 4H), 1.76-1.69 (m, 4H), 1.58-1.42 (m, 8H)

Step 2: Synthesis of Compound α

A four-necked reactor equipped with a thermometer was charged with 1.5 g (2.18 mmol) of the intermediate E, 2 ml of 2-propanol, and 5 ml of THF under a nitrogen stream to prepare a solution. After the addition of 80 mg (1.59 mmol) of hydrazine monohydrate to the solution, the mixture was stirred at 25° C. for 21 hours. After completion of the reaction, 2-propanol and THF were evaporated from the reaction mixture under reduced pressure using a rotary evaporator to obtain a yellow solid. The yellow solid was recrystallized from a mixed solvent (toluene:hexane=1:1), and a solid precipitate was filtered off, and washed with a mixed solvent (toluene:hexane=1:1). The resulting solid was purified by silica gel column chromatography (toluene:ethyl acetate=90:10 to 85:15 (gradient)) to obtain 1.1 g of a compound α as a light yellow solid (yield: 50.5%).

The structure of the target product was identified by $^1$H-NMR.

$^1$H-NMR (500 MHz, CDCl$_3$, TMS, δ ppm): 8.68 (s, 2H), 8.15 (d, 4H, J=9.0 Hz), 8.12 (d, 4H, J=9.0 Hz), 7.98 (d, 2H, J=3.0 Hz), 7.35 (dd, 2H, J=3.0 Hz, 9.0 Hz), 7.29 (d, 2H, J=9.0 Hz), 6.964 (d, 4H, J=9.0 Hz), 6.957 (d, 4H, J=9.0 Hz), 6.410 (dd, 2H, J=1.5 Hz, 17.5 Hz), 6.407 (dd, 2H, J=1.5 Hz, 17.5 Hz), 6.132 (dd, 2H, J=10.5 Hz, 17.5 Hz), 6.128 (dd, 2H, J=10.5 Hz, 17.5 Hz), 5.829 (dd, 2H, J=1.5 Hz, 10.5 Hz), 5.825 (dd, 2H, J=1.5 Hz, 10.5 Hz), 4.188 (t, 4H, J=6.5 Hz), 4.182 (t, 4H, J=6.5 Hz), 4.048 (t, 4H, J=6.5 Hz), 4.045 (t, 4H, J=6.5 Hz), 1.87-1.81 (m, 8H), 1.76-1.70 (m, 8H), 1.59-1.43 (m, 16H)

Example 2

0.4 g of the compound 1 obtained in Example 1, 0.6 g of a compound 1r ("LC242" manufactured by BASF) (see below), 30 mg of a photoinitiator ("Adekaoptomer N-1919" manufactured by Adeka Corporation), and 100 mg of a 1% cyclopentanone solution of a surfactant ("KH-40" manufactured by AGC Seimi Chemical Co., Ltd.) were dissolved in 2.3 g of cyclopentanone. The solution was filtered through a disposable filter having a pore size of 0.45 μm to prepare a polymerizable composition 1.

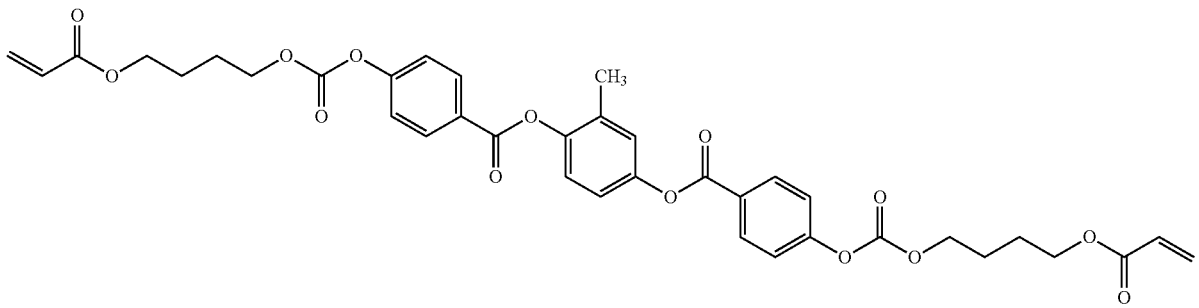

Compound 1r

Comparative Example 1

A polymerizable composition 2 was prepared substantially in the same manner as in Example 2, except that the compound α obtained in Synthesis Example 1 was used instead of the compound 1.

Comparative Example 2

A polymerizable composition 3 was prepared substantially in the same manner as in Example 2, except that 1.0 g of the compound α obtained in Synthesis Example 1 was used instead of the compound 1 (0.4 g) and the compound 1r (0.6 g).

Each of the polymerizable compositions 1 to 3 was polymerized using the following method to obtain a polymer. The retardation was measured, and the wavelength dispersion was evaluated using the resulting polymers.

Measurement of Retardation and Evaluation of Wavelength Dispersion (i) Formation of Liquid Crystal Layer Using Polymerizable Composition Each of the polymerizable compositions 1 to 3 was applied to a transparent glass substrate provided with a polyimide alignment film subjected to a rubbing treatment (manufactured by E.H.C. Co., Ltd.) using a #4 wire bar. The resulting film was dried for 1 minute at the temperature shown in Table 1, and subjected to an alignment treatment for 1 minute at the temperature shown in Table 1 to form a liquid crystal layer. Ultraviolet rays were applied to the liquid crystal layer at a dose of 2,000 mJ/cm$^2$ to effect polymerization to prepare a wavelength dispersion measurement sample.

(ii) Measurement of Retardation

The retardation between 400 nm and 800 nm was measured using the sample utilizing an ellipsometer ("M2000U" manufactured by J. A. Woollam).

(iii) Evaluation of Wavelength Dispersion

The wavelength dispersion was evaluated based on the values α and β that were calculated as described below using the measured retardation.

α=(retardation at 449.9 nm)/(retardation at 548.5 nm)
β=(retardation at 650.2 nm)/(retardation at 548.5 nm)

The value α is smaller than 1, and the value β is larger than 1 when ideal wideband wavelength dispersion (reverse wavelength dispersion) is achieved. The values α and β are almost identical to each other when flat wavelength dispersion is achieved. The value α is larger than 1, and the value β is smaller than 1 when normal dispersion is achieved.

Specifically, flat wavelength dispersion and reverse wavelength dispersion are preferable, and reverse wavelength dispersion is particularly preferable.

Table 1 shows the thickness (μm) of the liquid crystal polymer films obtained by polymerizing the polymerizable compositions, the retardation (Re) at a wavelength of 548.5 nm, and the values α and β.

TABLE 1

| | Polymerizable composition | Polymerizable compound Compound | Polymerizable compound Ratio (%) | Polymerizable compound Compound | Polymerizable compound Ratio (%) | Drying temperature (° C.) |
|---|---|---|---|---|---|---|
| Example 2 | 1 | 1 | 40 | 1r | 60 | 180 |
| Comparative Example 1 | 2 | α | 40 | 1r | 60 | 150 |
| Comparative Example 2 | 3 | — | — | 1r | 100 | 80 |

| | Alignment treatment temperature (° C.) | Temperature during exposure (° C.) | Thickness (μm) | Re (548.5 nm) | α | β |
|---|---|---|---|---|---|---|
| Example 2 | 160 | 150 | 1.493 | 183.5 | 0.959 | 1.001 |
| Comparative Example 1 | 130 | 130 | 1.503 | 205.6 | 1.035 | 0.988 |
| Comparative Example 2 | 23 | 23 | 1.479 | 222.9 | 1.086 | 0.970 |

As is clear from the results of Comparative Example 2, the compound 1r had normal dispersion since α>1 and β<1.

When the compound 1 obtained in Example 1 was added to the compound 1r (Example 2), reverse wavelength dispersion was obtained (i.e., α<1 and β>1).

When the compound α was added to the compound 1r (Comparative Example 1), reverse wavelength dispersion was not obtained (i.e., α>1 and β<1).

It was thus confirmed that a polymer that exhibits reverse wavelength dispersion can be obtained by polymerizing a polymerizable composition obtained by adding the compound according to one embodiment of the invention (compound 1) to a compound that exhibits normal wavelength dispersion.

The invention claimed is:

1. A polymerizable compound represented by a general formula (I),

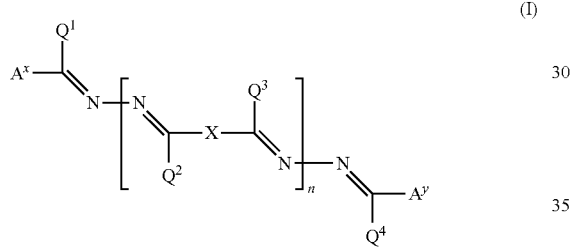

wherein each of $Q^1$ to $Q^4$ independently represents a hydrogen atom, or a substituted or unsubstituted alkyl group having 1 to 6 carbon atoms, X represents a substituted or unsubstituted divalent aromatic group having 4 to 12 carbon atoms, $A^x$ represents a group represented by a general formula (II),

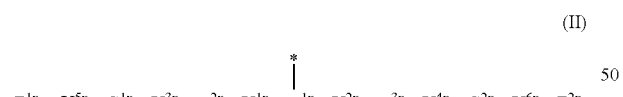

wherein "*" indicates a bonding position, each of $Y^{1x}$ to $Y^{6x}$ independently represents a single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, $R^1$ represents a hydrogen atom or an alkyl group having 1 to 6 carbon atoms, each of $G^{1x}$ and $G^{2x}$ independently represents a substituted or unsubstituted divalent aliphatic group having 1 to 20 carbon atoms that optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that a case where the aliphatic group includes two or more contiguous —O— or —S— is excluded, $R^2$ represents a hydrogen atom or an alkyl group having 1 to 6 carbon atoms, each of $Z^{1x}$ and $Z^{2x}$ independently represents an alkenyl group having 2 to 10 carbon atoms that is substituted with a halogen atom, or unsubstituted, $A^{1x}$ represents a substituted or unsubstituted trivalent aromatic group, and each of $A^{2x}$ and $A^{3x}$ independently represents a substituted or unsubstituted divalent aromatic group having 4 to 30 carbon atoms, $A^y$ represents a group represented by a general formula (III),

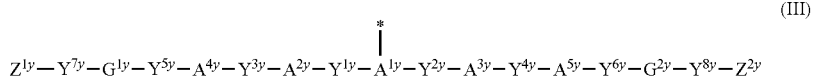

wherein each of $Y^{1y}$ to $Y^{8y}$ independently represents a single bond, —O—, —S—, —O—C(=O)—, —C(=O)—O—, —O—C(=O)—O—, —NR$^3$—C(=O)—, —C(=O)—NR$^3$—, —O—C(=O)—NR$^3$—, —NR$^3$—C(=O)—O—, —NR$^3$—C(=O)—NR$^3$—, —O—NR$^3$—, or —NR$^3$—O—, $R^3$ represents a hydrogen atom or an alkyl group having 1 to 6 carbon atoms, each of $G^{1y}$ and $G^{2y}$ independently represents a substituted or unsubstituted divalent aliphatic group having 1 to 20 carbon atoms that optionally includes —O—, —S—, —O—C(=O)—, —C(=O)—O—, —O—C(=O)—O—, —NR$^4$—C(=O)—, —C(=O)—NR$^4$—, —NR$^4$—, or —C(=O)—, provided that a case where the aliphatic group includes two or more contiguous —O— or —S— is excluded, $R^4$ represents a hydrogen atom or an alkyl group having 1 to 6 carbon atoms, each of $Z^{1y}$ and $Z^{2y}$ independently represents an alkenyl group having 2 to 10 carbon atoms that is substituted with a halogen atom, or unsubstituted, $A^{1y}$ represents a substituted or unsubstituted trivalent aromatic group, each of $A^{2y}$ and $A^{3y}$ independently represents a substituted or unsubstituted divalent alicyclic hydrocarbon group having 3 to 30 carbon atoms, and each of $A^{4y}$ and $A^{5y}$ independently represents a substituted or unsubstituted aromatic group having 4 to 30 carbon atoms, and n represents 0 or 1.

2. The polymerizable compound according to claim 1, wherein each of $A^{1x}$ and $A^{1y}$ is independently a substituted or unsubstituted trivalent benzene ring group, or a substituted or unsubstituted trivalent naphthalene ring group, and each of $A^{2x}$, $A^{3x}$, $A^{4y}$, and $A^{5y}$ is independently a substituted or unsubstituted phenylene group, or a substituted or unsubstituted naphthylene group.

3. The polymerizable compound according to claim 1, wherein each of $Y^{1x}$ to $Y^{6x}$ and $Y^{1y}$ to $Y^{8y}$ is independently a single bond, —O—, —O—C(=O)—, —C(=O)—O—, or —O—C(=O)—O—.

4. The polymerizable compound according to claim 1, wherein each of $Z^{1x}$, $Z^{2x}$, $Z^{1y}$ and $Z^{2y}$ is independently $CH_2=CH—$, $CH_2=C(CH_3)—$, or $CH_2=C(Cl)—$.

5. The polymerizable compound according to claim 1, wherein each of $G^{1x}$, $G^{2x}$, $G^{1y}$, and $G^{2y}$ is independently a substituted or unsubstituted divalent aliphatic group having 1 to 12 carbon atoms that optionally includes —O—, —O—C(=O)—, —C(=O)—O—, or —C(=O)—, provided that a case where the aliphatic group includes two or more contiguous —O— is excluded.

6. The polymerizable compound according to claim 1, wherein X is a substituted or unsubstituted phenylene group, a substituted or unsubstituted naphthylene group, or a substituted or unsubstituted biphenylene group.

7. The polymerizable compound according to claim 1, wherein each of $A^{1x}$ and $A^{1y}$ is independently a substituted or unsubstituted trivalent benzene ring group, each of $A^{2x}$, $A^{3x}$, $A^{4y}$, and $A^{5y}$ is independently a substituted or unsubstituted phenylene group, each of $Y^{1x}$ to $Y^{6x}$ and $Y^{1y}$ to $Y^{8y}$ is independently a single bond, , —O—, —O—C(=O)—, —C(=O)—O—, or —O—C(=O)—O—, each of $Z^{1x}$, $Z^{2x}$, $Z^{1y}$, $Z^{2y}$ is independently $CH_2$=CH—, $CH_2$=C($CH_3$)—, or $CH_2$=C(Cl)—, and each of $G^{1x}$, $G^{2x}$, $G^{1y}$, and $G^{2y}$ is independently a divalent alkylene group having 1 to 12 carbon atoms.

8. A polymerizable composition comprising at least one polymerizable compound according to claim 1, and an initiator.

9. A polymer obtained by polymerizing the polymerizable compound according to claim 1.

10. An optically anisotropic product comprising the polymer according to claim 9.

11. A polymer obtained by polymerizing the polymerizable composition according to claim 8.

12. An optically anisotropic product comprising the polymer according to claim 11.

13. The polymerizable compound according to claim 1, wherein the polymerizable compound is represented by a compound 1 compound 1

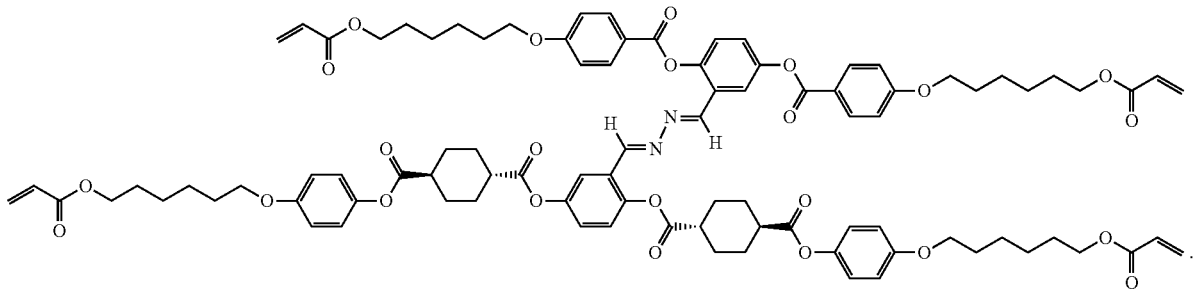

* * * * *